(12) United States Patent
Lins et al.

(10) Patent No.: US 7,918,875 B2
(45) Date of Patent: Apr. 5, 2011

(54) INTERSPINOUS DISTRACTION DEVICES AND ASSOCIATED METHODS OF INSERTION

(75) Inventors: Robert E. Lins, Boca Raton, FL (US);
Loren E. Lins, Boca Raton, FL (US);
Harvey Simovitch, Miami, FL (US)

(73) Assignee: Lanx, Inc., Broomfield, CO (US)

( * ) Notice: Subject to any disclaimer, the term of this patent is extended or adjusted under 35 U.S.C. 154(b) by 735 days.

(21) Appl. No.: 11/293,438

(22) Filed: Dec. 2, 2005

(65) Prior Publication Data
US 2006/0106397 A1  May 18, 2006

Related U.S. Application Data

(63) Continuation-in-part of application No. 11/257,647, filed on Oct. 25, 2005.

(60) Provisional application No. 60/633,112, filed on Dec. 3, 2004, provisional application No. 60/639,938, filed on Dec. 29, 2004, provisional application No. 60/654,483, filed on Feb. 21, 2005, provisional application No. 60/671,301, filed on Apr. 14, 2005, provisional application No. 60/678,360, filed on May 6, 2005, provisional application No. 60/621,712, filed on Oct. 25, 2004.

(51) Int. Cl.
*A61B 17/70* (2006.01)
(52) U.S. Cl. .................................. 606/248; 606/246
(58) Field of Classification Search .............. 606/248, 606/249, 246, 250, 251, 252, 253, 254, 255, 606/256, 257, 258, 259, 260, 261, 262, 263, 606/279; 623/17.11, 17.12–17.16
See application file for complete search history.

(56) References Cited

U.S. PATENT DOCUMENTS

| | | | |
|---|---|---|---|
| 2,677,369 A | 4/1954 | Knowles | |
| 2,789,860 A | 4/1957 | Knowles | |
| 4,092,788 A | 6/1978 | Gowing | |
| 4,369,770 A | 1/1983 | Bacal et al. | |
| 4,409,968 A | 10/1983 | Drummond | |
| 4,448,191 A | 5/1984 | Rodnyansky et al. | |
| 4,599,086 A * | 7/1986 | Doty ............................ | 606/86 A |
| 4,892,545 A * | 1/1990 | Day et al. .................... | 623/17.11 |

(Continued)

FOREIGN PATENT DOCUMENTS

EP    1 266 606 A2    12/2002

(Continued)

OTHER PUBLICATIONS

Article: An Interspinous Process Distractor (X Stop) for Lumbar Spinal Stenosis in Elderly Patients by Jangbo Lee, MD, Kazutoshi Hida, MD, Toshitaka Seki, MD, Yoshinobu Iwasaki, MD.

(Continued)

*Primary Examiner* — Eduardo C Robert
*Assistant Examiner* — Jan Christopher Merene
(74) *Attorney, Agent, or Firm* — Holland & Hart LLP

(57) ABSTRACT

In various embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

17 Claims, 48 Drawing Sheets

U.S. PATENT DOCUMENTS

| | | | |
|---|---|---|---|
| 5,010,879 A | 4/1991 | Moriya et al. | |
| 5,062,850 A * | 11/1991 | MacMillan et al. | 623/17.11 |
| 5,496,318 A | 3/1996 | Howland et al. | |
| 5,503,617 A | 4/1996 | Jako | |
| 5,645,599 A | 7/1997 | Samani | |
| 5,658,335 A | 8/1997 | Allen | |
| 5,800,550 A | 9/1998 | Sertich | |
| 5,813,978 A | 9/1998 | Jako | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,045,552 A | 4/2000 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,277,094 B1 | 8/2001 | Schendel | |
| 6,280,444 B1 | 8/2001 | Zucherman et al. | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,416,776 B1 | 7/2002 | Shamie | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,500,178 B2 | 12/2002 | Zucherman et al. | |
| 6,514,256 B2 | 2/2003 | Zucherman et al. | |
| 6,520,907 B1 | 2/2003 | Foley | |
| 6,582,433 B2 | 6/2003 | Zucherman et al. | |
| 6,599,294 B2 | 7/2003 | Fuss et al. | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,679,833 B2 | 1/2004 | Smith et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,733,534 B2 | 5/2004 | Sherman | |
| 6,746,485 B1 | 6/2004 | Zucherman et al. | |
| 6,761,720 B1 | 7/2004 | Senegas | |
| 6,796,983 B1 | 9/2004 | Zucherman et al. | |
| 6,800,084 B2 | 10/2004 | Davison et al. | |
| 6,902,566 B2 | 6/2005 | Zucherman et al. | |
| 6,926,728 B2 | 8/2005 | Zucherman et al. | |
| 6,946,000 B2 * | 9/2005 | Senegas et al. | 623/17.11 |
| 6,966,929 B2 | 11/2005 | Mitchell | |
| 6,989,011 B2 | 1/2006 | Paul et al. | |
| 7,029,473 B2 | 4/2006 | Zucherman et al. | |
| 7,083,649 B2 | 8/2006 | Zucherman et al. | |
| 7,585,316 B2 * | 9/2009 | Trieu | 606/279 |
| 7,753,938 B2 * | 7/2010 | Aschmann et al. | 606/248 |
| 2001/0007070 A1 | 7/2001 | Zuckerman at al. | |
| 2001/0016743 A1 | 8/2001 | Zuckerman et al. | |
| 2001/0016776 A1 | 8/2001 | Zuckerman et al. | |
| 2001/0021850 A1 | 9/2001 | Zuckerman et al. | |
| 2001/0031965 A1 * | 10/2001 | Zuckerman et al. | 606/61 |
| 2001/0039452 A1 | 11/2001 | Zuckerman et al. | |
| 2002/0183746 A1 | 12/2002 | Zucherman et al. | |
| 2003/0065330 A1 | 4/2003 | Zucherman et al. | |
| 2003/0153915 A1 | 8/2003 | Nekozuka | |
| 2003/0216736 A1 | 11/2003 | Robinson et al. | |
| 2004/0138749 A1 | 7/2004 | Zucherman et al. | |
| 2004/0138750 A1 | 7/2004 | Mitchell | |
| 2004/0143270 A1 | 7/2004 | Zucherman et al. | |
| 2004/0147937 A1 | 7/2004 | Dunbar | |
| 2004/0153071 A1 | 8/2004 | Zucherman et al. | |
| 2004/0162617 A1 | 8/2004 | Zucherman et al. | |
| 2004/0167520 A1 | 8/2004 | Zucherman et al. | |
| 2004/0172135 A1 | 9/2004 | Mitchell | |
| 2004/0193159 A1 | 9/2004 | Zucherman et al. | |
| 2004/0199121 A1 | 10/2004 | Wenchell | |
| 2004/0220568 A1 | 11/2004 | Zucherman et al. | |
| 2004/0249379 A1 | 12/2004 | Winslow et al. | |
| 2005/0010296 A1 | 1/2005 | Mitchell | |
| 2005/0010298 A1 | 1/2005 | Zucherman et al. | |
| 2005/0101955 A1 | 5/2005 | Zucherman et al. | |
| 2005/0113926 A1 | 5/2005 | Zucherman et al. | |
| 2005/0125065 A1 | 6/2005 | Zucherman et al. | |
| 2005/0143738 A1 | 6/2005 | Zucherman et al. | |
| 2005/0143820 A1 | 6/2005 | Zucherman et al. | |
| 2005/0143826 A1 | 6/2005 | Zucherman et al. | |
| 2005/0149192 A1 | 7/2005 | Zucherman et al. | |
| 2005/0149193 A1 | 7/2005 | Zucherman et al. | |
| 2005/0149196 A1 | 7/2005 | Zucherman et al. | |
| 2005/0154456 A1 | 7/2005 | Zucherman et al. | |
| 2005/0192586 A1 | 9/2005 | Zucherman et al. | |
| 2005/0196420 A1 | 9/2005 | Zucherman et al. | |
| 2005/0209603 A1 | 9/2005 | Zucherman et al. | |
| 2005/0216087 A1 | 9/2005 | Zucherman et al. | |
| 2005/0228383 A1 | 10/2005 | Zucherman et al. | |
| 2005/0228384 A1 | 10/2005 | Zucherman et al. | |
| 2005/0261768 A1 | 11/2005 | Trieu | |
| 2006/0015099 A1 | 1/2006 | Cannon et al. | |
| 2007/0032790 A1 * | 2/2007 | Aschmann et al. | 606/61 |
| 2007/0049943 A1 * | 3/2007 | Moskowitz et al. | 606/72 |
| 2007/0225706 A1 * | 9/2007 | Clark et al. | 606/61 |
| 2007/0233076 A1 * | 10/2007 | Trieu | 606/61 |

FOREIGN PATENT DOCUMENTS

| | | |
|---|---|---|
| JP | 2003220071 A | 8/2003 |
| WO | WO 94/00062 | 1/1994 |
| WO | WO 2005/009300 A1 | 2/2005 |

OTHER PUBLICATIONS

International Bureau, Notification Concerning Transmittal of International Preliminary Report on Patentability (Chapter 1 of the Patent Cooperation Treaty), May 10, 2007.

Kyphon "X-Stop A Patients's Guide Lumber Spinal Stenosis & X-Stop Interspinous Decompression".

Jeremy C Wang, MD Regis W. Haid Jr., M.D. Jay S. Miller, M.D. and James C. Robinson, M.D. "Comparison of CD Horizon Spire spinous process plate stabilization and pedicle screw fixation after anterior lumbar interbody fusion" Feb. 4, 2006.

Jeremy C Wang, MD., David Spenciner, P.E., Sc.M., and James C. Robinson, M.D. "Spire spinous process stabilization plate: biochemical evaluation of a novel technology" Feb. 4, 2006.

Ole Bostman, Pertti Myllynen & Erik B. Riska "Posterior spinal fusion using internal fixation with the Daab plate" pp. 310-314 1984.

F.L. Knowles "The Knowles Vertebral Support Orientation" pp. 551-554, Oct. 1958.

Kyphon X-Stop IPD System "The first minimally invasive solution to lumbar spine stenosis".

* cited by examiner

Note: Basic Cross-Sectional Shape May Be Semi-Circular, Rectangular, Square, Etc. All Floors Are Also Optional.

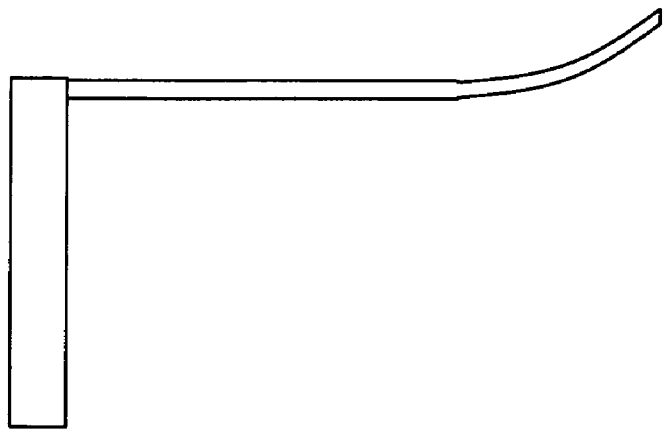
44
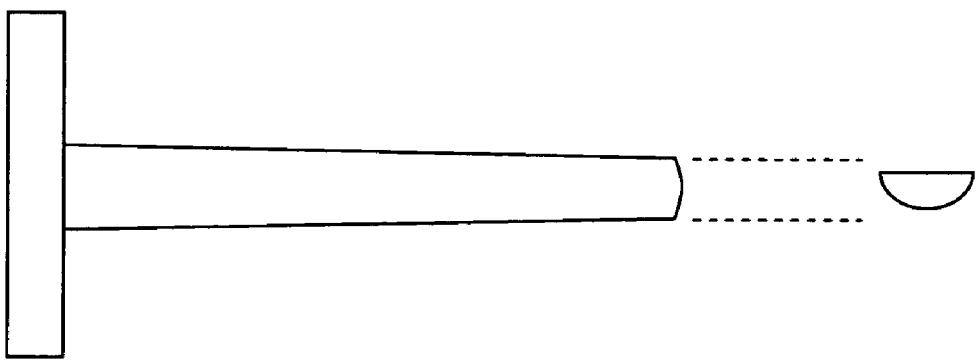
FIG. 10.

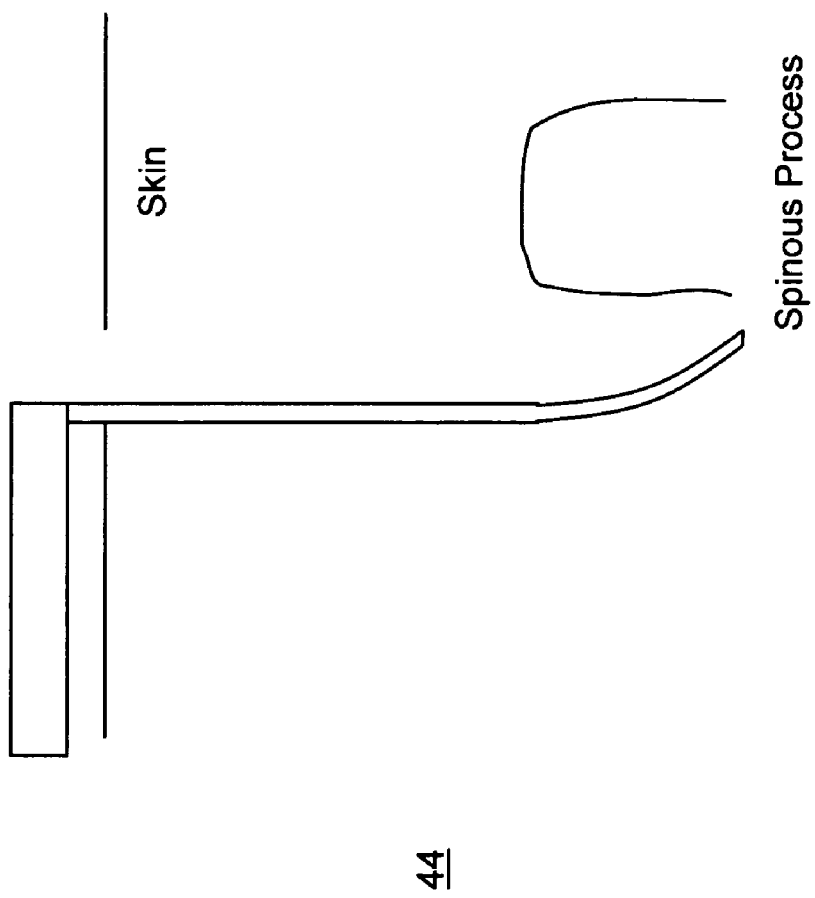
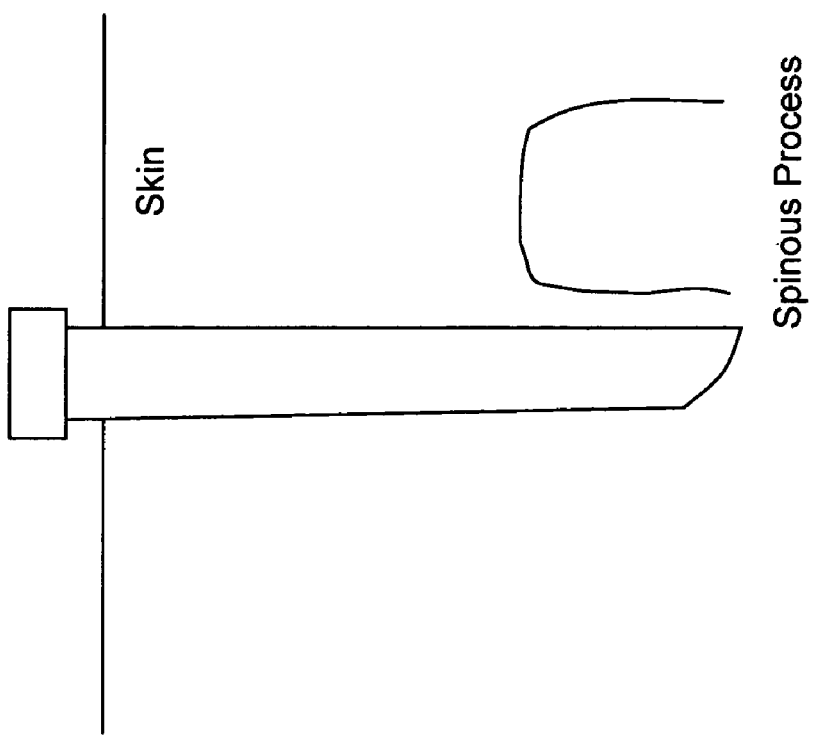
FIG. 11.

Optionally, Shape of Inflated Distraction Bladder
Allows for Adjacent Placement

Line Guides Associated With
Pre-Threaded Line Attached to
Bladder are Inserted Into Wound
Through Guide Tube Note: All Line Guides are Optionally
Biocompatible and are Left in Wound

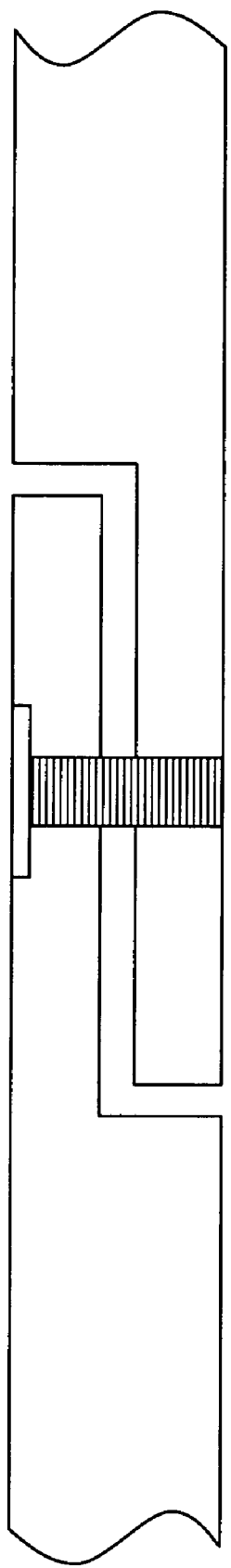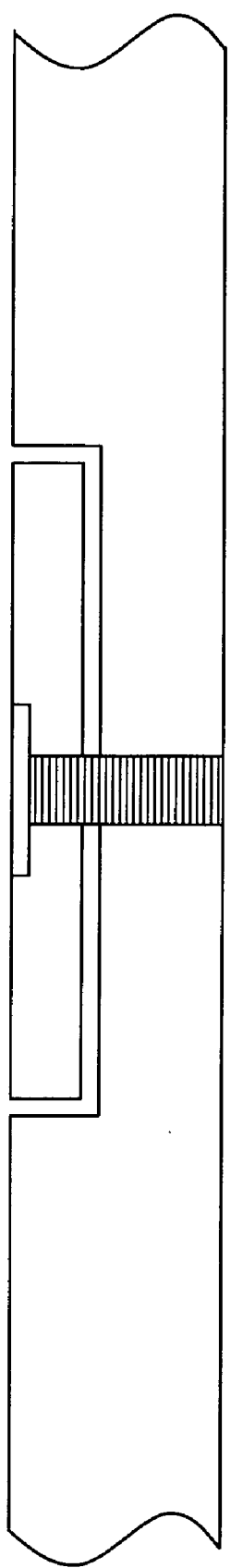
Preferably, All Screw and Cold-Weld Configurations Are Flush-Mounted
*FIG. 41.*

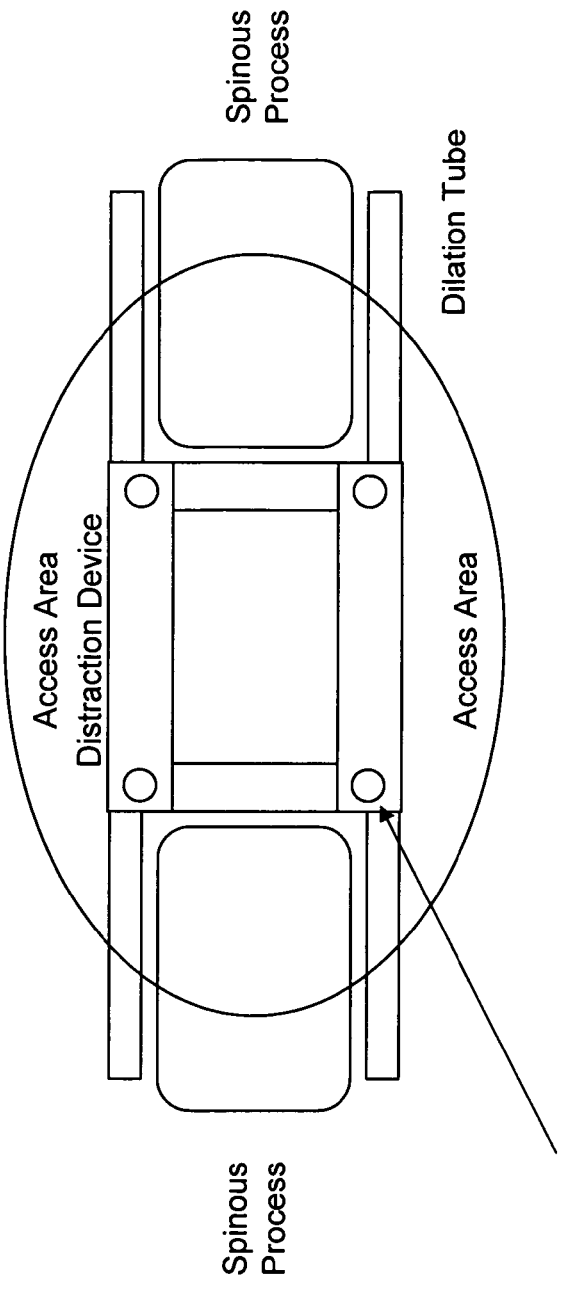
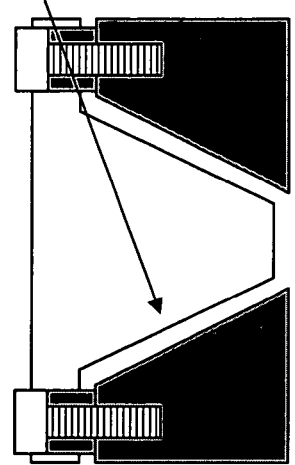
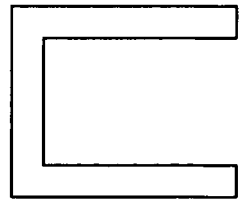
FIG. 46.

INTERSPINOUS DISTRACTION DEVICES AND ASSOCIATED METHODS OF INSERTION

CROSS-REFERENCE TO RELATED APPLICATION(S)

The present non-provisional patent application claims the benefit of priority of U.S. Provisional Patent Application No. 60/633,112, entitled "INTERSPINOUS DISTRACTION DEVICES AND ASSOCIATED METHODS OF INSERTION," and filed on Dec. 3, 2004; U.S. Provisional Patent Application No. 60/639,938, entitled "INTERSPINOUS DISTRACTION DEVICES AND ASSOCIATED METHODS OF INSERTION," and filed on Dec. 29, 2004; U.S. Provisional Patent Application No. 60/654,483, entitled "INTERSPINOUS DISTRACTION DEVICES AND ASSOCIATED METHODS OF INSERTION," and filed on Feb. 21, 2005; U.S. Provisional Patent Application No. 60/671,301, entitled "INTERSPINOUS DISTRACTION DEVICES AND ASSOCIATED METHODS OF INSERTION," and filed on Apr. 14, 2005; and U.S. Provisional Patent Application No. 60/678,360, entitled "INTERSPINOUS DISTRACTION DEVICES AND ASSOCIATED METHODS OF INSERTION," and filed on May 6, 2005, each of which is incorporated in full by reference herein. The present non-provisional patent application is a continuation-in-part of U.S. patent application Ser. No. 11/257,647, entitled "INTERSPINOUS DISTRACTION DEVICES AND ASSOCIATED METHODS OF INSERTION," and filed on Oct. 25, 2005, which claims the benefit of priority of U.S. Provisional Patent Application No. 60/621,712, entitled "INTERSPINOUS DISTRACTION DEVICES AND ASSOCIATED METHODS OF INSERTION," and filed on Oct. 25, 2004; U.S. Provisional Patent Application No. 60/633,112, entitled "INTERSPINOUS DISTRACTION DEVICES AND ASSOCIATED METHODS OF INSERTION," and filed on Dec. 3, 2004; U.S. Provisional Patent Application No. 60/639,938, entitled "INTERSPINOUS DISTRACTION DEVICES AND ASSOCIATED METHODS OF INSERTION," and filed on Dec. 29, 2004; U.S. Provisional Patent Application No. 60/654,483, entitled "INTERSPINOUS DISTRACTION DEVICES AND ASSOCIATED METHODS OF INSERTION," and filed on Feb. 21, 2005; U.S. Provisional Patent Application No. 60/671,301, entitled "INTERSPINOUS DISTRACTION DEVICES AND ASSOCIATED METHODS OF INSERTION," and filed on Apr. 14, 2005; and U.S. Provisional Patent Application No. 60/678,360, entitled "INTERSPINOUS DISTRACTION DEVICES AND ASSOCIATED METHODS OF INSERTION," and filed on May 6, 2005, each of which is incorporated in full by reference herein.

FIELD OF THE INVENTION

The present invention relates generally to the medical and surgical fields. More specifically, the present invention relates to a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

BACKGROUND OF THE INVENTION

Lumbar spinal stenosis is characterized by a tightening of or decrease in the cross-sectional diameter of the spinal canal and neural foramen, through which the spinal cord and nerve roots of the lumbar (lower) spine pass, caused by the degeneration of the lumbar discs (through fluid loss and collapse) and the facet joints of the spinal column. In lumbar spinal stenosis, the lumbar discs deteriorate and the lumbar disc spaces collapse, resulting in a portion of the lumbar discs protruding into the ventral or anterior (front) portion of the spinal canal. At the same time, the two facet joints associated with each lumbar vertebrae become arthritic, growing in size, and protruding into the dorsal or posterior (back) portion of the spinal canal. Thus, the cross-sectional diameter of the spinal canal is decreased, impinging on the spinal cord and nerve roots of the lumbar spine. In addition, the ligamentum flavum that connect the bases of the spinous processes of the spinal column and the lamina tend to buckle with lumbar disc collapse, further decreasing the cross-sectional diameter of the spinal canal. The neural foramen, through which the nerve roots exit, are pinched with disc collapse and facet joint arthropathy. This condition is especially common in the elderly and symptoms may include remitting or unremitting pain and/or weakness/numbness in the middle to lower back and/or legs when moving or stationary. It should be noted that similar problems can occur in the cervical (upper) spine as well.

Conventional treatments for lumbar spinal stenosis include oral or injectable analgesic and/or anti-inflammatory medications (non-steroidal or steroidal), activity avoidance and/or physical therapy, braces, and surgical procedures. Surgical procedures for lumbar spinal stenosis include laminectomies/laminotomies and spinal fusions. In a laminectomy/laminotomy, all or a portion of a given facet joint, lamina, and ligamentum flavum is removed to alleviate compression of the spinal canal. This procedure basically "unroofs" or enlarges a portion of the spinal canal. Additionally, a spinal fusion may be performed. In a spinal fusion, a connecting bar and a bone graft are used to join or fuse adjacent vertebrae via a plurality of pedicle screws, thus stabilizing the vertebral segment. Much, if not all, of a given lumbar disc is removed in conjunction with a spinal fusion. In general, a spinal fusion is most suitable when there is instability or translation between adjacent vertebrae (spondylolisthesis). Disadvantageously, the plurality of pedicle screws used to perform a spinal fusion may become loose with the passage of time if a nonunion develops. Both laminectomies/laminotomies and spinal fusions are major, open procedures, typically requiring a relatively large incision and a general anesthetic. This may be dangerous for the elderly or the sick. In addition, both procedures are very expensive.

What has been observed clinically is that many patients, when they flex forward, experience an increase in the cross-sectional diameter of the spinal canal and neural foramen, thus alleviating or eliminating their pain and/or weakness/numbness caused by lumbar spinal stenosis. This is caused by the temporary distraction of the spinous processes and the "stretching out" of the ligamentum flavum that connect the bases of the spinous processes and lamina. The collapsed neural foramen are also increased in height and cross-sectional area by the distraction. In other words, the lumbar discs and other structures of the spinal column are temporarily decompressed. This observation has led to improved treatments for lumbar spinal stenosis.

The interspinous process distractor (X Stop) for lumbar spinal stenosis disclosed and described by Lee et al. (J. Spinal Disord. Tech., Vol. 17, No. 1, February 2004) provides a main body assembly including a spacer and a universal wing assembly. The main body assembly is disposed between adjacent interspinous processes, distracting them, and the universal wing assembly is used to lock the main body assembly in place. Because the interspinous process distractor utilizes a nut that must be engaged and tightened, the interspinous process distractor must be inserted using a conventional open procedure. Again, this may be dangerous for the elderly or the sick and requires a general anesthetic.

Relatively young patients with lumbar disc degeneration and facet arthropathy may present with back pain. If conservative treatment is ineffective, these patients may require a lumbar fusion or total disc arthroplasty. By decreasing the pressure on the disc and facet joints both in a neutral and extension stance, an interspinous spacer may present a less invasive, reversible alternative.

Thus, what is needed are simple, inexpensive interspinous distraction devices and associated methods of insertion that are designed and configured to effectively treat such conditions as lumbar spinal stenosis and degenerative disc disease. The interspinous distraction devices should be capable of being inserted through conventional open procedures, typically requiring a relatively large incision and a general anesthetic, or through novel minimally-invasive procedures, typically requiring only a local anesthetic.

BRIEF SUMMARY OF THE INVENTION

In various embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures and related enabling devices are also disclosed and described herein.

In one specific embodiment of the present invention, an interspinous distraction device for treating such conditions as lumbar spinal stenosis and degenerative disc disease includes a body assembly configured to be disposed between adjacent spinous processes of the spinal column of a patient, wherein the body assembly is sized such that the body assembly distracts the adjacent spinous processes apart. The interspinous distraction device also includes a plurality of attachment arms extending outwardly from the body assembly, the plurality of attachment arms configured to be disposed about a portion of each of the adjacent spinous processes and securely hold the body assembly in place relative to each of the adjacent spinous processes of the spinal column of the patient.

In another specific embodiment of the present invention, a dilation tube system for providing minimally-invasive surgical access to a portion of the spinal column or the like includes a hollow dilation tube having a first end, a second end, a given cross-sectional shape, and a longitudinal axis, wherein the first end of the dilation tube includes a cut-away portion for providing access from an interior portion of the dilation tube to an exterior portion of the dilation tube in a direction perpendicular to the longitudinal axis of the dilation tube. The dilation tube system also includes a hollow guide tube having a first end, a second end, a given cross-sectional shape, and a longitudinal axis disposed concentrically within the dilation tube, wherein the first end of the dilation tube includes an elbow portion for providing access from an interior portion of the guide tube to an exterior portion of the guide tube in a direction perpendicular to the longitudinal axis of the guide tube through the cut-away portion of the dilation tube. The dilation tube system further includes a plurality of additional hollow dilation tubes having graduated diameters.

In a further specific embodiment of the present invention, a method for inserting an interspinous distraction device for treating such conditions as lumbar spinal stenosis and degenerative disc disease includes disposing a body assembly between adjacent spinous processes of the spinal column of a patient, wherein the body assembly is sized such that the body assembly distracts the adjacent spinous processes apart. The method for inserting the interspinous distraction device also includes extending a plurality of attachment arms outwardly from the body assembly, the plurality of attachment arms disposed about a portion of each of the adjacent spinous processes and securely holding the body assembly in place relative to each of the adjacent spinous processes of the spinal column of the patient. Optionally, the body assembly is disposed between adjacent spinous processes of the spinal column of the patient through a hollow dilation tube having a first end, a second end, a given cross-sectional shape, and a longitudinal axis, wherein the first end of the dilation tube includes a cut-away portion for providing access from an interior portion of the dilation tube to an exterior portion of the dilation tube in a direction perpendicular to the longitudinal axis of the dilation tube. Optionally, the body assembly is also disposed between adjacent spinous processes of the spinal column of the patient through a hollow guide tube having a first end, a second end, a given cross-sectional shape, and a longitudinal axis disposed concentrically within the dilation tube, wherein the first end of the dilation tube includes an elbow portion for providing access from an interior portion of the guide tube to an exterior portion of the guide tube in a direction perpendicular to the longitudinal axis of the guide tube through the cut-away portion of the dilation tube.

In a still further embodiment of the present invention, an interspinous distraction device for treating such conditions as lumbar spinal stenosis and degenerative disc disease includes a body assembly of either solid material or cured polymer configured to be disposed between adjacent spinous processes of the spinal column of a patient, wherein the body assembly is sized such that the body assembly distracts the adjacent spinous processes apart. The interspinous distraction device also includes a band configured to be disposed about the adjacent spinous processes of the spinal column of the patient and engage the body assembly, wherein the band is sized such that the adjacent spinous processes are stabilized with respect to one another.

In a still further embodiment of the present invention, an interspinous distraction device for treating such conditions as lumbar spinal stenosis and degenerative disc disease includes an extensible body assembly configured to be disposed between adjacent spinous processes of the spinal column of a patient, wherein the body assembly is sized such that the body assembly distracts the adjacent spinous processes apart. The interspinous distraction device also includes a plurality of attachment arms extending outwardly from the body assembly, the plurality of attachment arms configured to be disposed about a portion of each of the adjacent spinous processes and securely hold the body assembly in place relative to each of the adjacent spinous processes of the spinal column of the patient.

BRIEF DESCRIPTION OF THE DRAWINGS

The present invention is illustrated and described herein with reference to various figures, in which like reference numbers denote like components and/or parts, and in which:

FIG. 10 is a planar view illustrating a further alternative embodiment of the dilation tube system of the present invention, with sequential solid semicircular dilation rods on the left and a "shoehorn"-type device on the right to assist in the placement of the dilation tube, the dilation tube system used to insert the interspinous distraction devices of FIGS. 1-4, 7, and 12-23 into the spinal column of a patient;

FIG. 11 is a planar view illustrating the dilation tube system of FIG. 10 in operation;

FIG. 41 is a partial cross-sectional side view of a plurality of flush-mount configurations of the present invention;

FIG. 46 is a top planar and cross-sectional side view of a full-access "impacted screw H" distraction device of the present invention;

DETAILED DESCRIPTION OF THE INVENTION

In various embodiments, the present invention provides a plurality of novel interspinous distraction devices and associated methods of insertion. The interspinous distraction devices of the present invention are designed and configured to effectively treat such conditions as lumbar spinal stenosis and degenerative disc disease. Advantageously, the interspinous distraction devices of the present invention may be inserted through conventional open procedures, typically requiring a relatively large incision and a general anesthetic, or through novel minimally-invasive procedures, typically requiring only a local anesthetic. These novel minimally-invasive procedures, and related enabling devices, are also disclosed and described herein.

Figure 1:
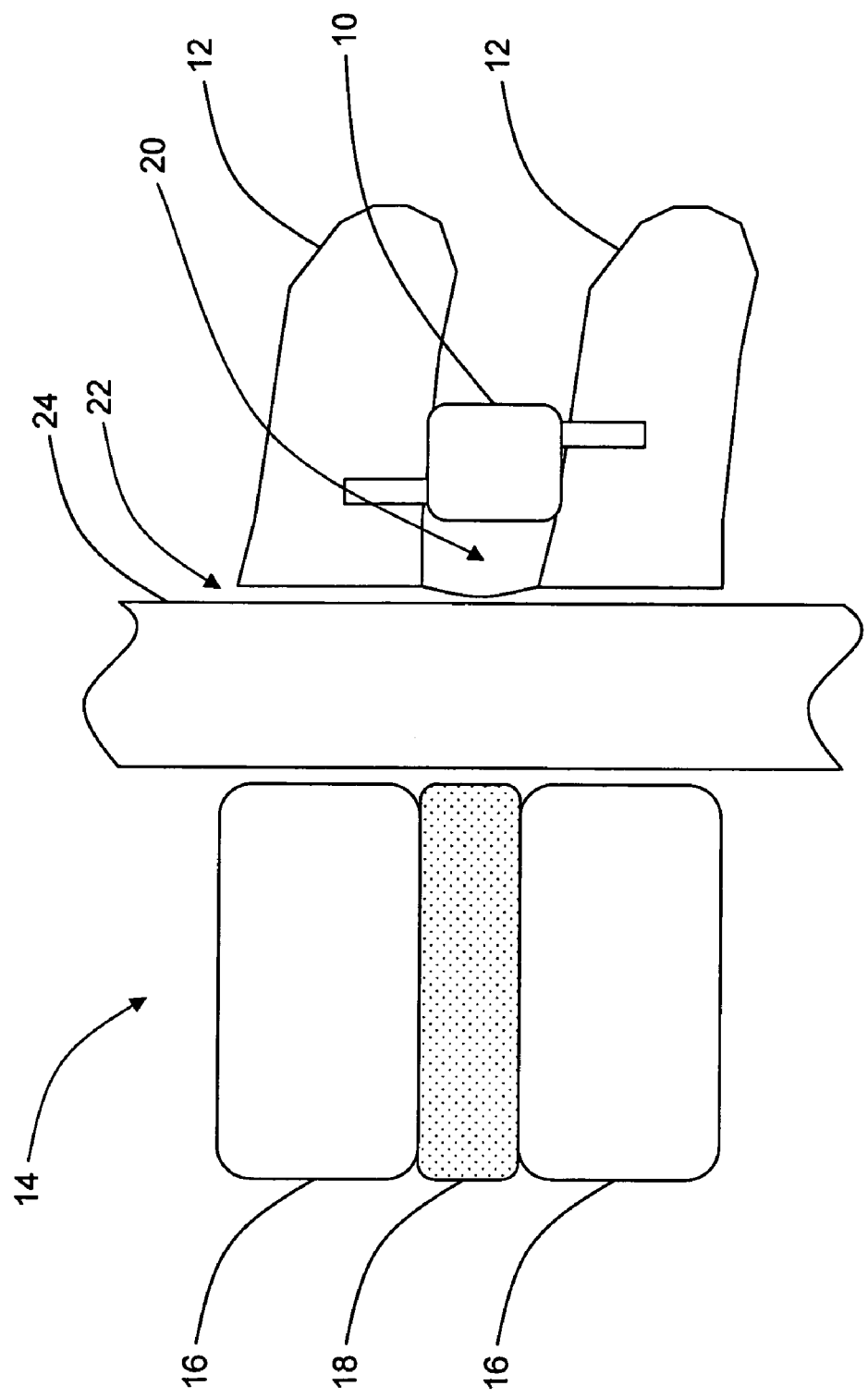
FIG. 1 is a cross-sectional side view illustrating the spinal column of a patient and the placement of one embodiment of the interspinous distraction device of the present invention.

Referring now to FIG. 1, in one specific embodiment, the interspinous distraction device 10 of the present invention is disposed between adjacent spinous processes 12 of the spinal column 14 of a patient. The spinal column 14 also includes a plurality of vertebral bodies 16 present on a plurality of levels of the lumbar (lower) and cervical (upper) spine and a plurality of discs 18 separating the plurality of vertebral bodies 16. It is these discs 18 and the facet joints 20 associated with the ligamentum flavum that deteriorate and protrude into the spinal canal 22, impinging on the spinal cord 24 and neural foramen, in conditions such as lumbar spinal stenosis. The interspinous distraction device 10 is sized such that it distracts adjacent spinous processes 12 apart, alleviating the protrusion and impingement described above.

Figure 2:
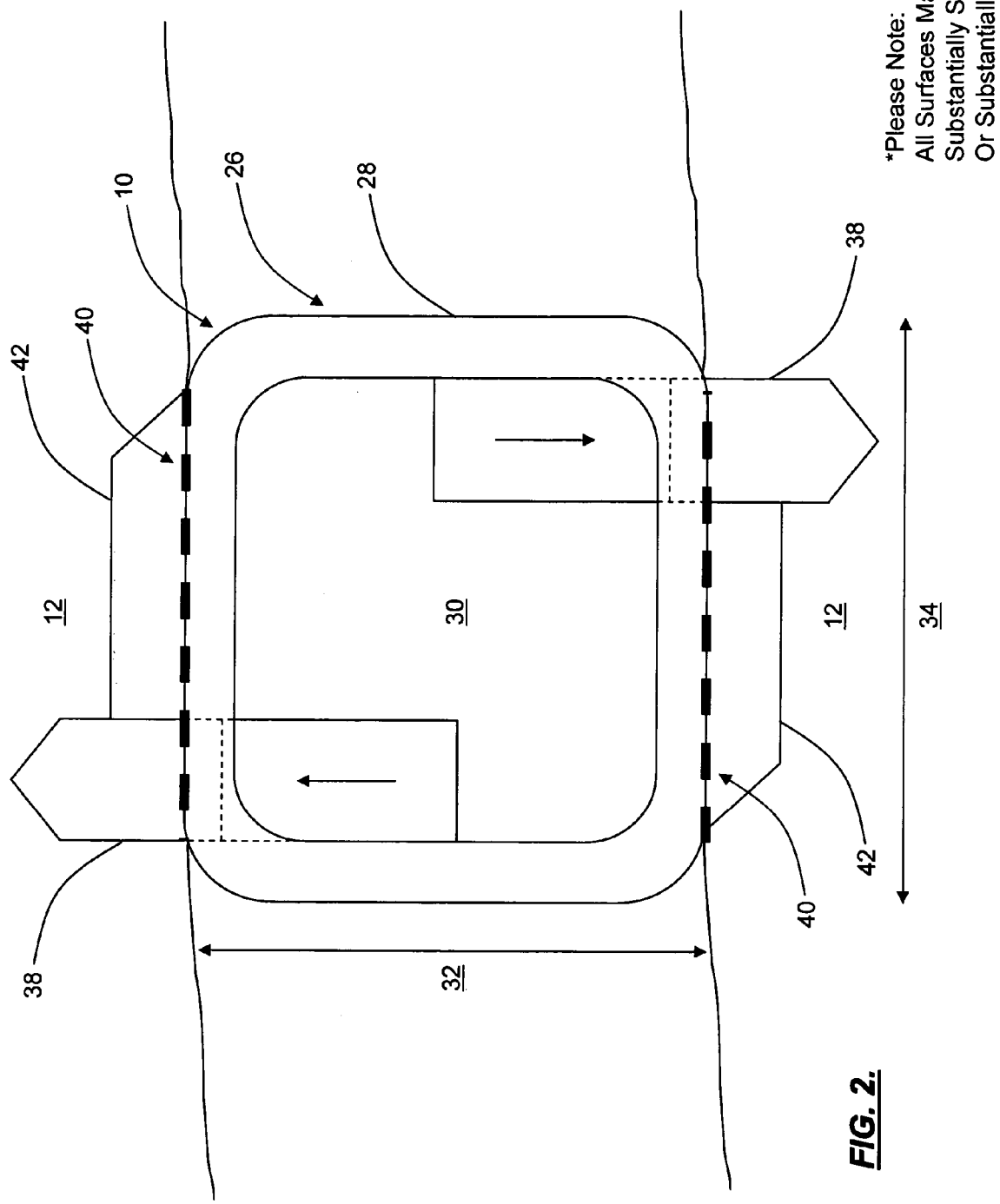
FIG. 2 is a cross-sectional side view illustrating one embodiment of the interspinous distraction device of the present invention.
Figure 3:
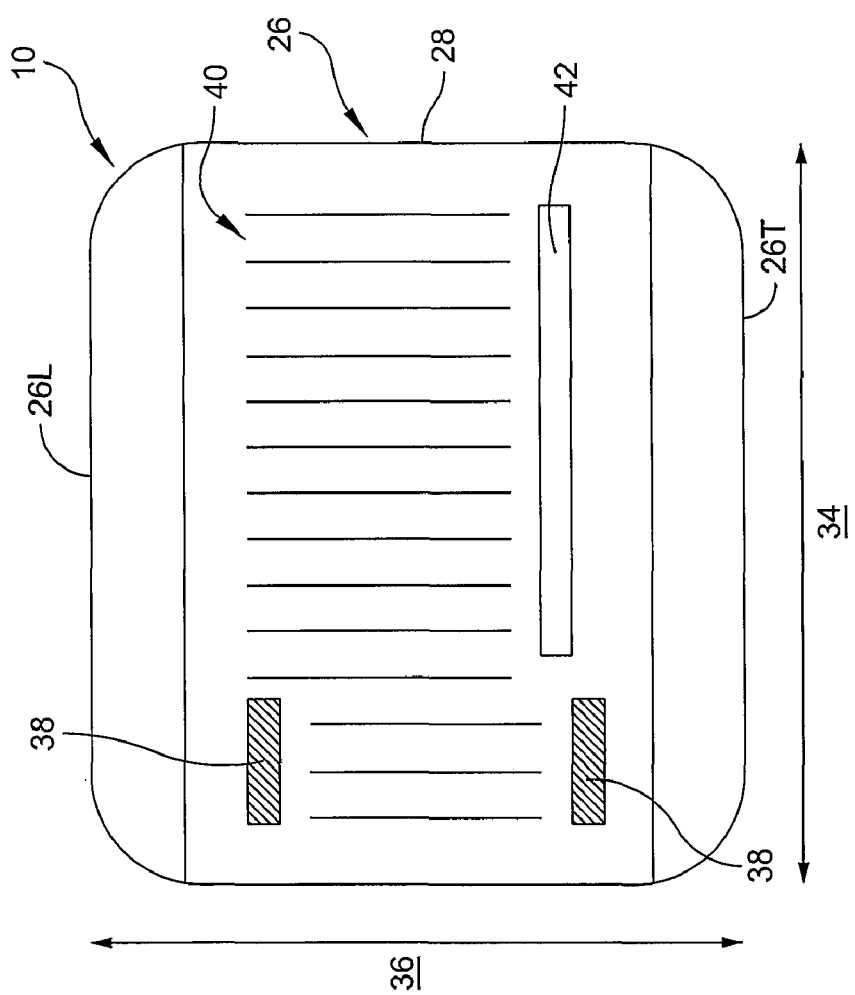
FIG. 3 is a planar top view illustrating the interspinous distraction device of FIG. 2.
Figure 4:
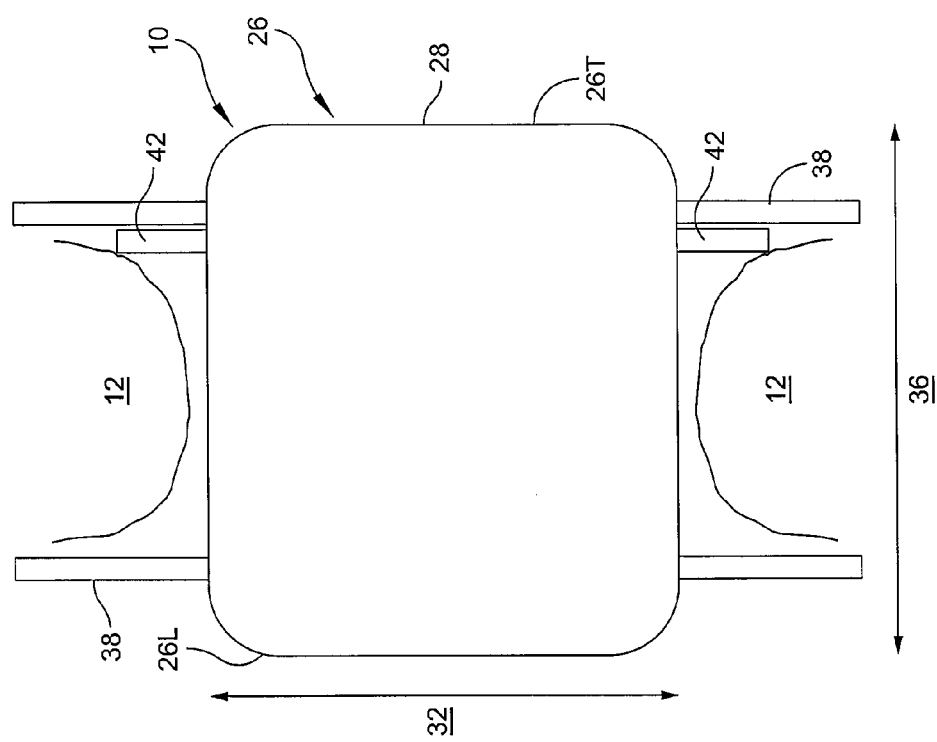
FIG. 4 is a planar front view illustrating the interspinous distraction device of FIGS. 2 and 3.

Referring now to FIGS. 2-4, the interspinous distraction device 10 of the present invention includes a body assembly 26 consisting of a circumferential wall 28 defining an interior void 30. The body assembly 26 has a shape that is substantially rectangular, substantially square, substantially oval, substantially circular, a combination thereof, or any other suitable shape. The body assembly 26 has a height 32 of between about 4 mm and about 20 mm, a width 34 of between about 10 mm and about 25 mm, and a thickness 36 of between about 10 mm and about 20 mm. Preferably, the body assembly 26 and other components of the interspinous distraction device 10 are made of a medically-implantable, corrosion-resistant metal; a medically-implantable, corrosion-resistant metal alloy; a medically-implantable plastic; a medically-implantable ceramic; or a combination thereof.

The body assembly 26 of the interspinous distraction device 10 also includes a plurality of attachment arms 38 extending outwardly from the circumferential wall 28 of the body assembly 26, the plurality of attachment arms 38 configured to be disposed about a portion of each of the adjacent spinous processes 12 and securely hold the body assembly 26 in place relative to each of the adjacent spinous processes 12. Preferably, each of the plurality of attachment arms 38 is at least partially disposed within the interior void 30 defined by the circumferential wall 28 of the body assembly 26 and is selectively extendable outwardly from/retractable inwardly into the interior void 30. Each of the plurality of attachment arms 38 has a length of between about 4 mm and about 20 mm. In one exemplary embodiment of the interspinous distraction device 10 of the present invention, the plurality of attachment arms 38 resemble a plurality of staple-like structures. Optionally, the body assembly 26 of the interspinous distraction device 10 incorporates a filler plug (not shown) selectively disposed within the interior void 30 defined by the circumferential wall 28 when the plurality of attachment arms 38 have been extended.

The body assembly 26 of the interspinous distraction device 10 further includes one or more friction surfaces 40 consisting of one or more ridged surfaces, one or more grooved surfaces, one or more corrugated surfaces, one or more pebbled surfaces, or a combination thereof, the one or more friction surfaces 40 configured to securely hold the body assembly 26 in place relative to each of the adjacent spinous processes 12.

The body assembly 26 of the interspinous distraction device 10 still further includes one or more fin structures 42 also configured to securely hold the body assembly 26 in place relative to each of the adjacent spinous processes 12. Specifically, the one or more fin structures 42 prevent the body assembly 26 from "overshooting" the gap between the adjacent spinous processes 12 when the interspinous distraction device 10 is inserted. A leading end 26L and a trailing end 26T may be in opposition to one another. (See FIGS. 3 and 4.) Leading end 26L is configured to be on one side of the adjacent spinous processes 12 and traling end 26 T is configured to be disposed on another side of the adjacent spinous processes 12. The one or more fin structures 42 may be of any suitable size and/or shape to achieve this purpose.

Although one specific embodiment of the interspinous distraction device 10 of the present invention has been illustrated and described above, other embodiments may perform similar functions and/or achieve similar results. For example, the body assembly 26 and the plurality of attachment arms 38 of the interspinous distraction device 10 may be configured such that the plurality of attachment arms 38 rotatably engage the adjacent spinous processes 12 when the body assembly 26 is rotated.

Figure 5:
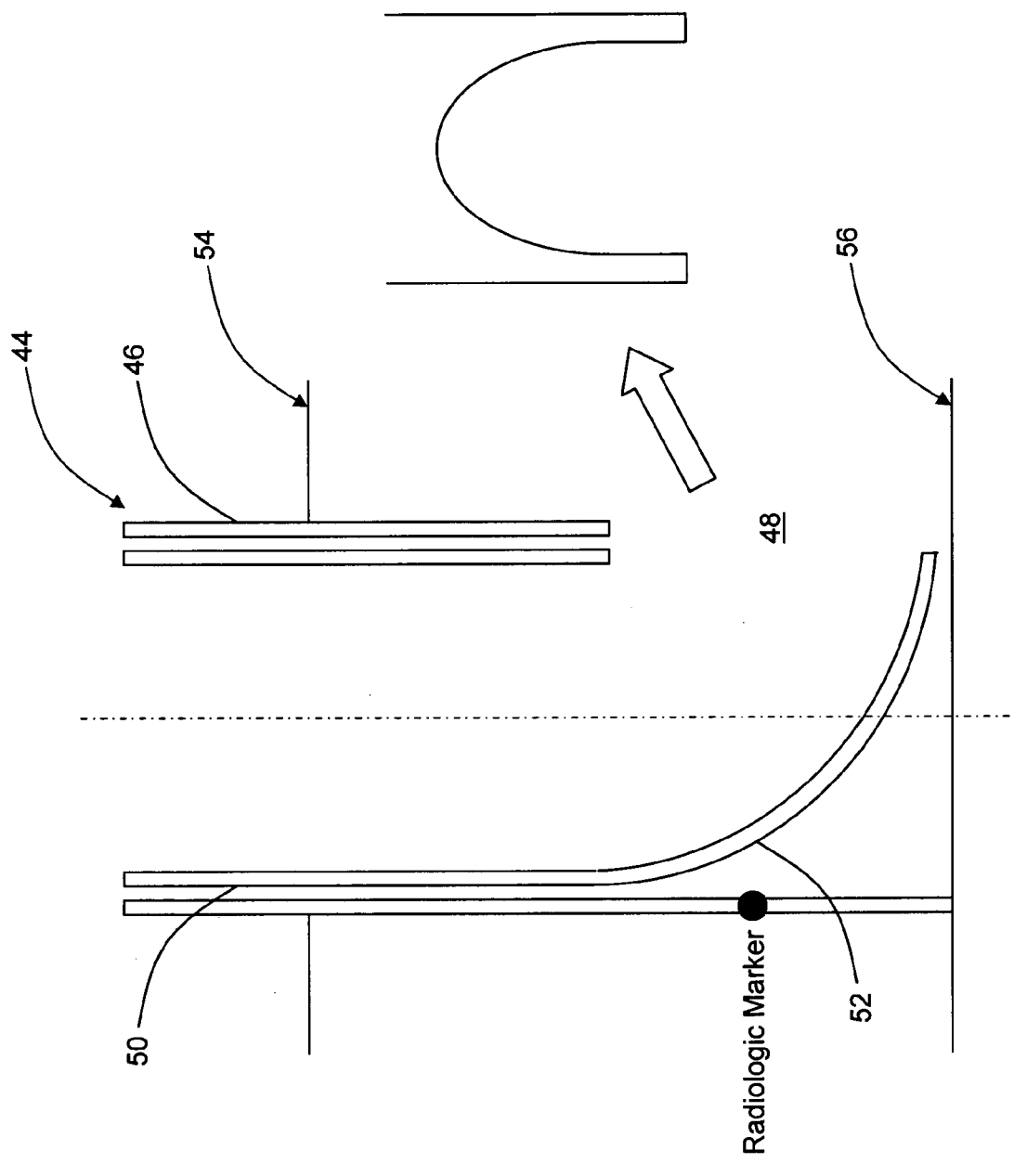
FIG. 5 is a longitudinal cross-sectional side view illustrating one embodiment of the dilation tube system of the present invention, the dilation tube system used to insert the interspinous distraction device of FIGS. 2-4 into the spinal column of a patient.

Referring now to FIG. 5, in one specific embodiment, the dilation tube system 44 of the present invention provides minimally-invasive surgical access to a portion of the spinal column or the like. The dilation tube system 44 includes a hollow dilation tube 46 having a first end, a second end, a given cross-sectional shape, and a longitudinal axis. The first end of the dilation tube 46 includes a cut-away portion 48 for providing access from an interior portion of the dilation tube 46 to an exterior portion of the dilation tube 46 in a direction perpendicular to the longitudinal axis of the dilation tube 46.

The dilation tube system 44 also includes a hollow guide tube 50 having a first end, a second end, a given cross-sectional shape, and a longitudinal axis. The hollow guide tube 50 is disposed concentrically within the dilation tube 46. The first end of the guide tube 50 includes an elbow portion 52 for providing access from an interior portion of the guide tube 50 to an exterior portion of the guide tube 50 in a direction perpendicular to the longitudinal axis of the guide tube 50 through the cut-away portion 48 of the dilation tube 46.

The dilation tube 46 and the guide tube 50 each have a cross-sectional shape that is substantially circular, substantially semi-circular, substantially oval, substantially square, substantially rectangular, substantially triangular, a combination thereof, or any other suitable shape. The dilation tube 46 and the guide tube 50 each have a diameter of between about 18 mm and about 22 mm. The dilation tube 46 and the guide tube 50 are each made of a material such as a medically-implantable, corrosion-resistant metal; a medically-implantable, corrosion-resistant metal alloy; a medically-implantable plastic; a medically-implantable ceramic; a combination thereof; or the like.

Figure 9:
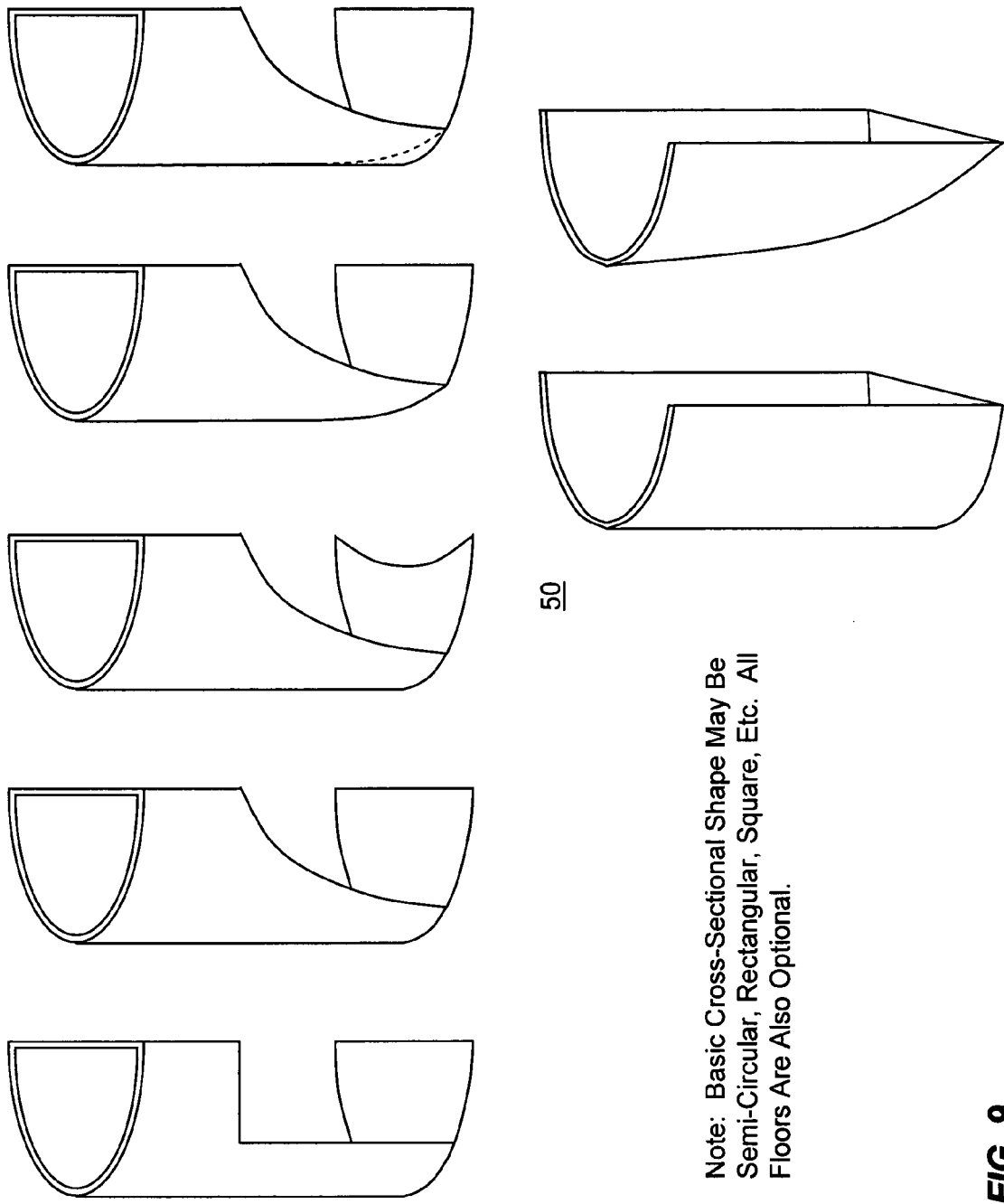
FIG. 9 is a perspective view illustrating a plurality of alternative embodiments of the dilation tube system of the present invention, and, specifically, a plurality of alternative embodiments of the guide tube of the present invention, the dilation tube system allowing wider surgical access at the base and used to insert the interspinous distraction devices of FIGS. 1-4, 7, and 12-23 into the spinal column of a patient.

Referring now to FIG. 9, a plurality of alternative embodiments of the dilation tube system 44 of the present invention are provided, and, specifically, a plurality of alternative embodiments of the guide tube 50 of the present invention, the dilation tube system 44 allowing wider surgical access at the base and used to insert the interspinous distraction devices of FIGS. 1-4, 7, and 12-23 into the spinal column of a patient.

Referring now to FIGS. 10 and 11, a further alternative embodiment of the dilation tube system 44 of the present invention is provided. The dilation tube system 44 includes a plurality of sequentially-sized and inserted solid dilation rods (FIGS. 10 and 11 left), each of the solid dilation rods having a slight taper and smoothed edges. The solid dilation rods each have a cross-sectional shape that is substantially circular, substantially semi-circular, substantially oval, substantially square, substantially rectangular, substantially triangular, a combination thereof, or any other suitable shape. One of the various guide tubes 50 described above is inserted into a patient's back using a "shoehorn"-type device, as illustrated in FIGS. 10 and 11 right.

Referring again to FIG. 5, in operation, the dilation tube 46 and the guide tube 50 are inserted through the skin 54 of a patient, as described in greater detail below, and seated in an area of interest or on a surface of interest 56. The dilation tube 46 provides access to the area of interest and the cut-away portion 48 of the dilation tube 46 provides access to the area of interest in a direction perpendicular to the longitudinal axis of the dilation tube 46. Likewise, the guide tube 50 provides access to the area of interest and the elbow portion 52 of the guide tube 50 provides access to the area of interest in a direction perpendicular to the longitudinal axis of the guide tube 50. In other words, the dilation tube 46 and the guide tube 50 of the present invention provide novel lateral access to an area of interest. Advantageously, the elbow portion 52 of the guide tube 50 helps to guide devices and instruments inserted through the guide tube 50 into a lateral position for placement. Optionally, the dilation tube 46 and the guide tube 50 are integrally formed or combined.

Figure 6:
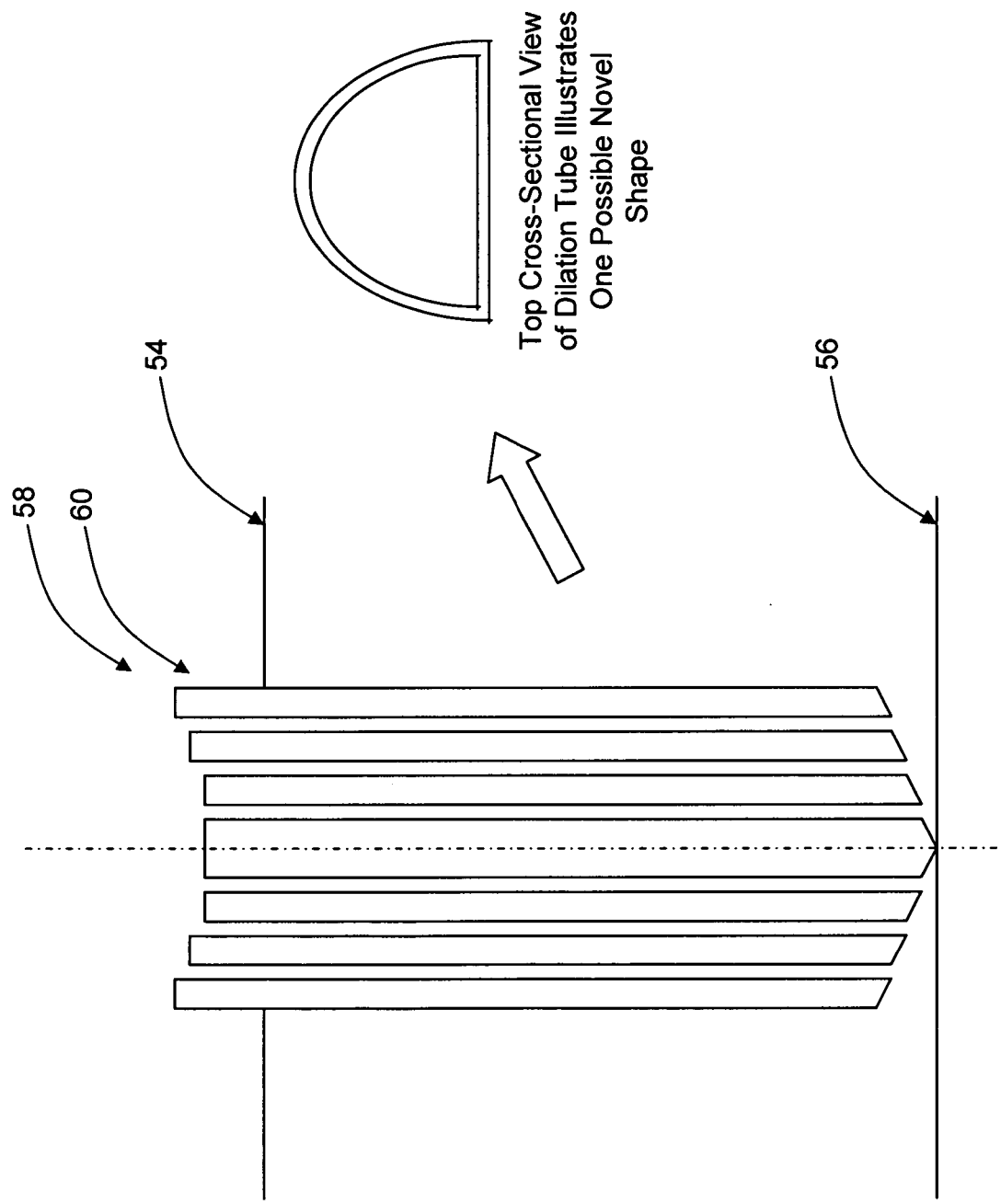
FIG. 6 is a longitudinal cross-sectional side view illustrating a conventional dilation tube system used in conjunction with the dilation tube system of FIG. 5.

Referring now to FIG. 6, the dilation tube system 44 of the present invention is preferably used in conjunction with a conventional dilation tube system 58, well known to those of ordinary skill in the art, that includes a plurality of additional dilation tubes 60, each of the plurality of additional dilation tubes 60 having a diameter that is smaller than the diameter of the dilation tube 46 of the present invention. Each of the plurality of additional dilation tubes 60 is selectively and temporarily disposed concentrically within a space or hole of increasing diameter that is eventually large enough to receive the dilation tube 46 and guide tube 50 of the present invention.

In one specific embodiment of the present invention, a method for inserting the interspinous distraction device 10 (FIGS. 2-4) described above includes disposing the body assembly 26 (FIG. 2-4) described above between adjacent spinous processes 12 (FIG. 1-4) of the spinal column 14 (FIG. 1) of a patient. Again, the body assembly 26 is sized such that the body assembly 26 distracts the adjacent spinous processes 12 apart. The method also includes extending the plurality of attachment arms 38 (FIGS. 2-4) described above outwardly from the body assembly 26, the plurality of attachment arms 38 disposed about a portion of each of the adjacent spinous processes 12 and securely holding the body assembly 26 in place relative to each of the adjacent spinous processes 12 of the spinal column 14 of the patient. The body assembly 26 is disposed between adjacent spinous processes 12 of the spinal column 14 of the patient through the dilation tube 46 (FIG. 5) and the guide tube 50 (FIG. 5) described above.

Figure 7:
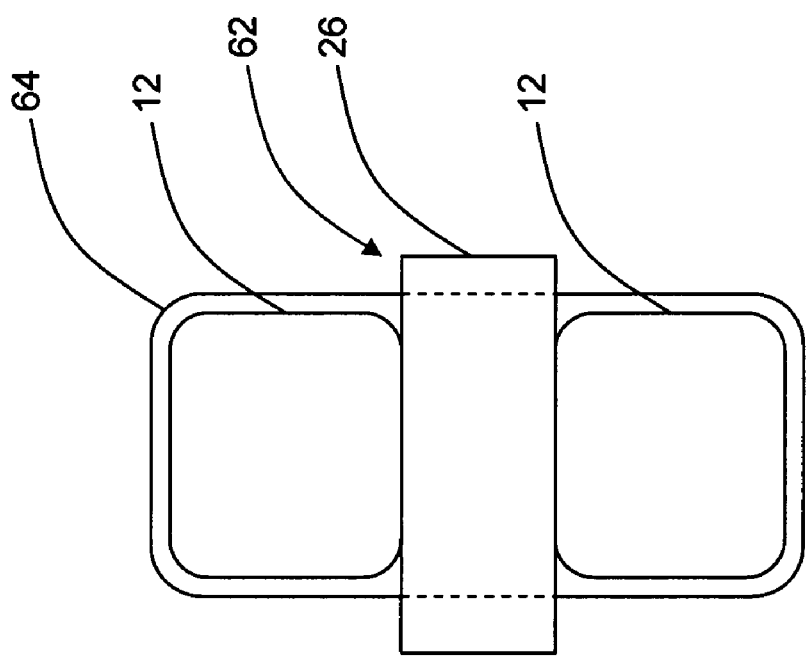
FIG. 7 a planar dorsal or anterior (back) view illustrating another embodiment of the interspinous distraction device of the present invention, the interspinous distraction device incorporating a stabilizing band.

Referring now to FIG. 7, in an alternative embodiment of the present invention, an interspinous distraction device 62 for treating such conditions as lumbar spinal stenosis and degenerative disc disease includes a body assembly 26 configured to be disposed between adjacent spinous processes 12 of the spinal column 14 (FIG. 1) of a patient. Again, the body assembly 26 is sized such that the body assembly 26 distracts the adjacent spinous processes 12 apart. The body assembly 26 may be the same as that described above, incorporating a plurality of attachment arms 38 (FIGS. 2-4), etc., or it may be a simple anchored or floating spacer device. The interspinous distraction device 62 also includes a band 64 configured to be disposed about the adjacent spinous processes 12 of the spinal column 14 of the patient and engage the body assembly 26, via crimping or otherwise. Thus, the band may initially be a simple strip of medically-implantable material or it may be a closed loop of medically-implantable material. The band 64 is sized such that the adjacent spinous processes 12 are stabilized with respect to one another. The band 64 maybe be substantially elastic or non-elastic and typically has a circumferential length of between about 60 mm and about 150 mm. The interspinous distraction device 62 is inserted into the spinal column 14 of the patient using an open procedure.

Figure 8:
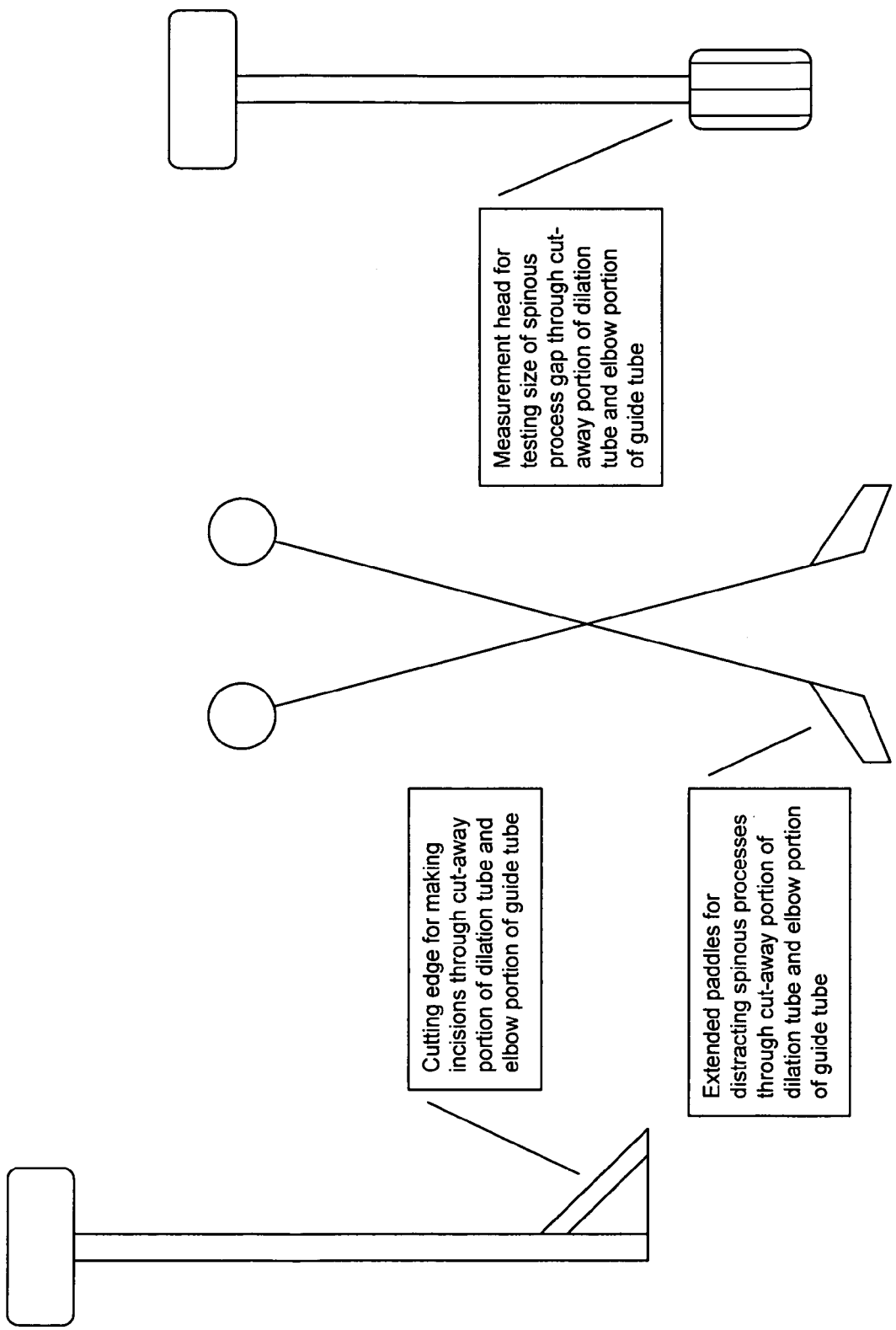
FIG. 8 is a planar view illustrating a plurality of enabling tools and instruments used in conjunction with the interspinous distraction devices of the present invention.

The present invention also contemplates a plurality of enabling tools and instruments. Such tools include extended handles and holding tools for feeding the interspinous distraction device 10 (FIGS. 2-4) through the dilation tube 46 (FIG. 5) and guide tube (FIG. 5) and anchoring the interspinous distraction device 10 between the adjacent spinous processes (FIG. 1). Such tools also include actuating and ratcheting tools for engaging the plurality of attachment arms 38 (FIGS. 2-4) of the interspinous distraction device 10 and placing the filler plug (not shown) in the interior void 30 (FIG. 2) defined by the circumferential wall 28 (FIGS. 2-4) of the body assembly 26 (FIGS. 2-4) of the interspinous distraction device 10, for example. Such tools further include visualization and cutting tools for preparing and distracting the area of interest for receiving the interspinous distraction device 10, including hinged, retractor-like, distraction tools. Several of these tools are illustrated in FIG. 8.

Figure 12:
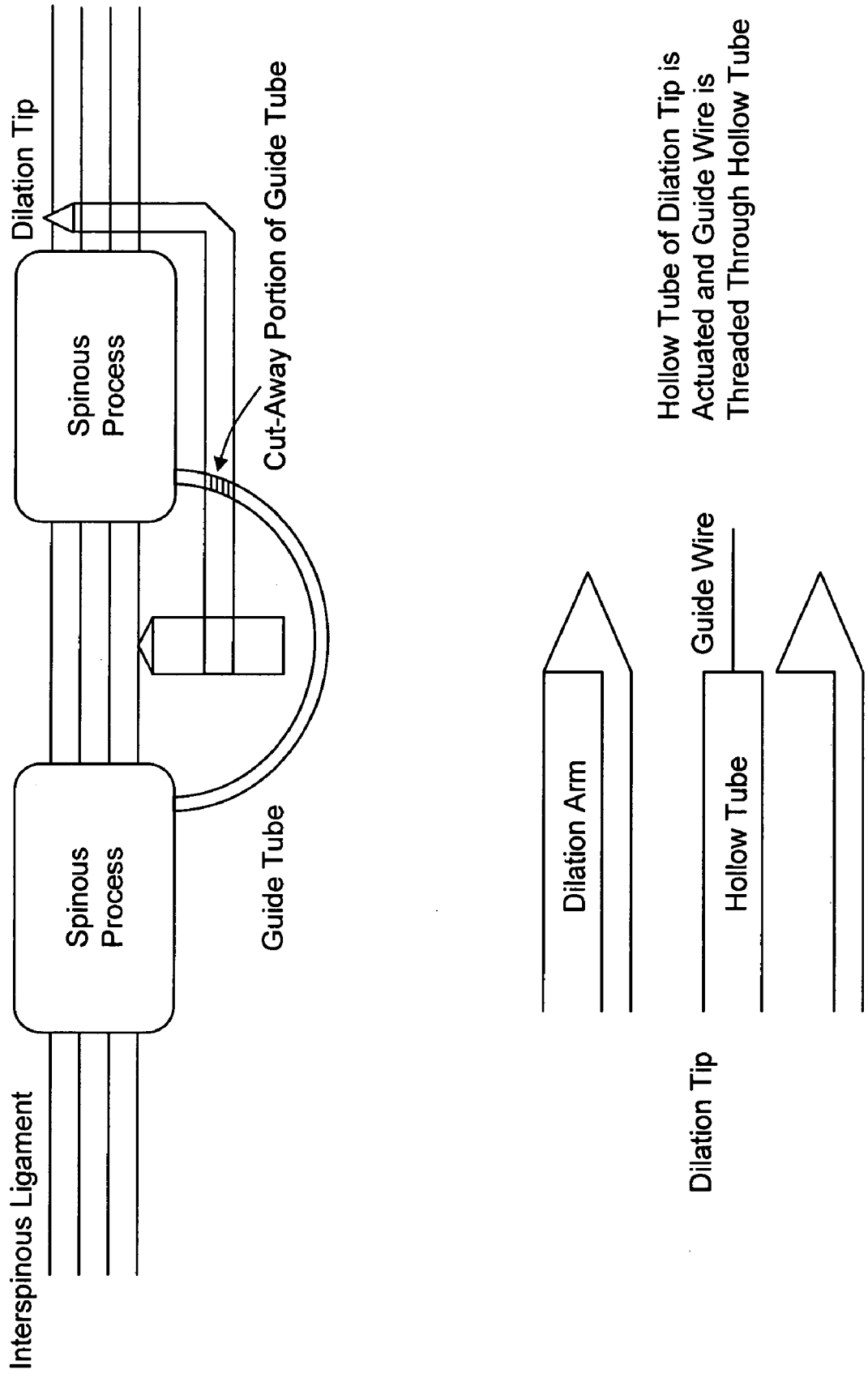
FIG. 12 is a planar view illustrating one aspect/step of an alternative embodiment of an interspinous distraction system and an associated minimally-invasive method of insertion, the interspinous distraction system utilizing a polymer-filled packet and a tension band.
Figure 13:
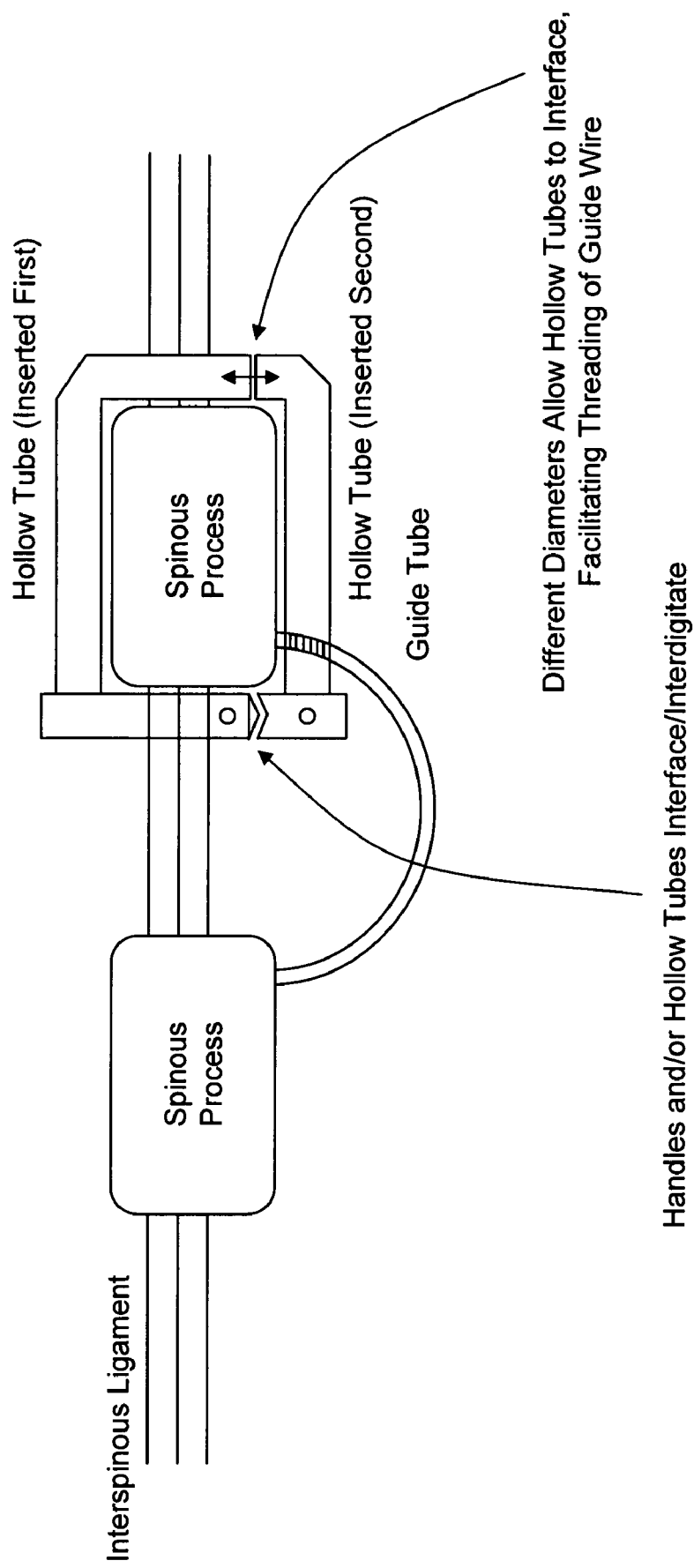
FIG. 13 is a planar view illustrating another aspect/step of the interspinous distraction system and the associated minimally-invasive method of insertion of FIG. 12.
Figure 14:
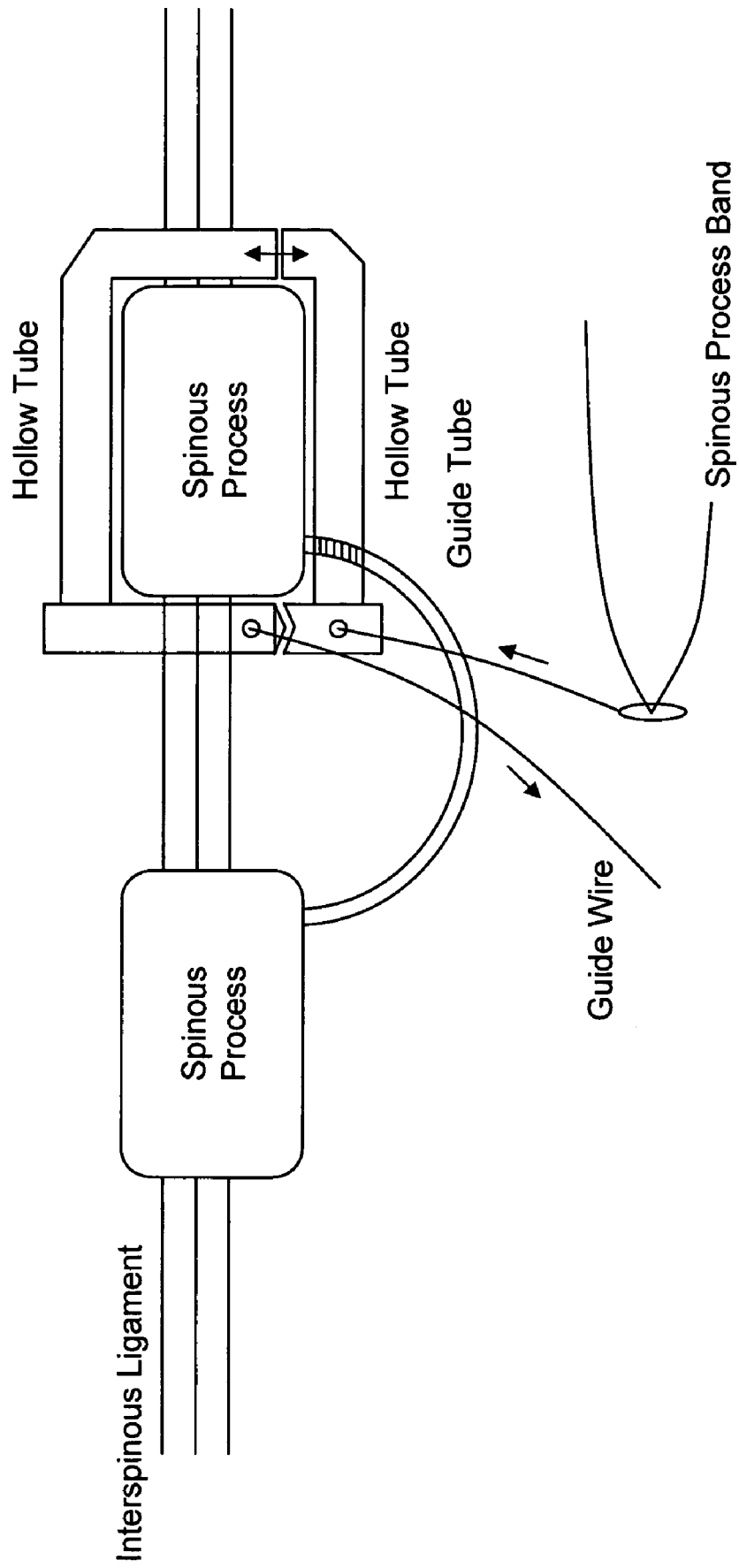
FIG. 14 is a planar view illustrating a further aspect/step of the interspinous distraction system and the associated minimally-invasive method of insertion of FIGS. 12 and 13.
Figure 15:
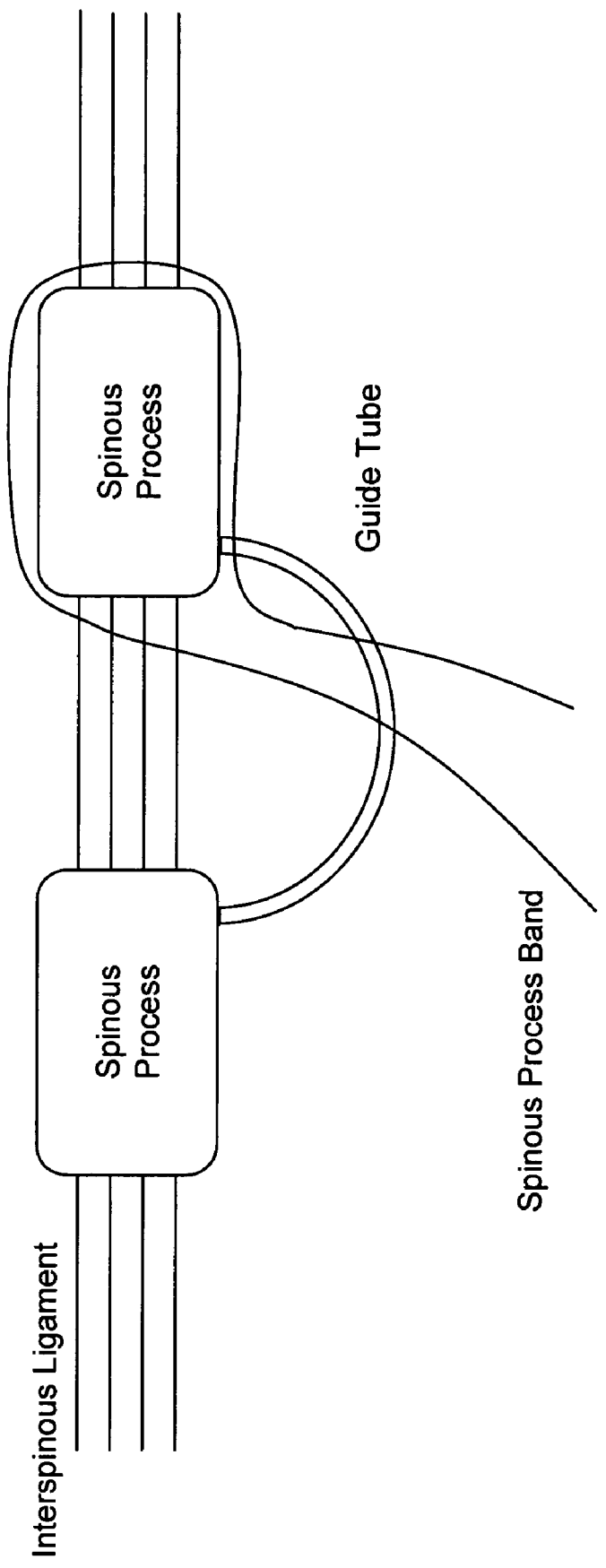
FIG. 15 is a planar view illustrating a still further aspect/step of the interspinous distraction system and the associated minimally-invasive method of insertion of FIGS. 12-14.
Figure 16:
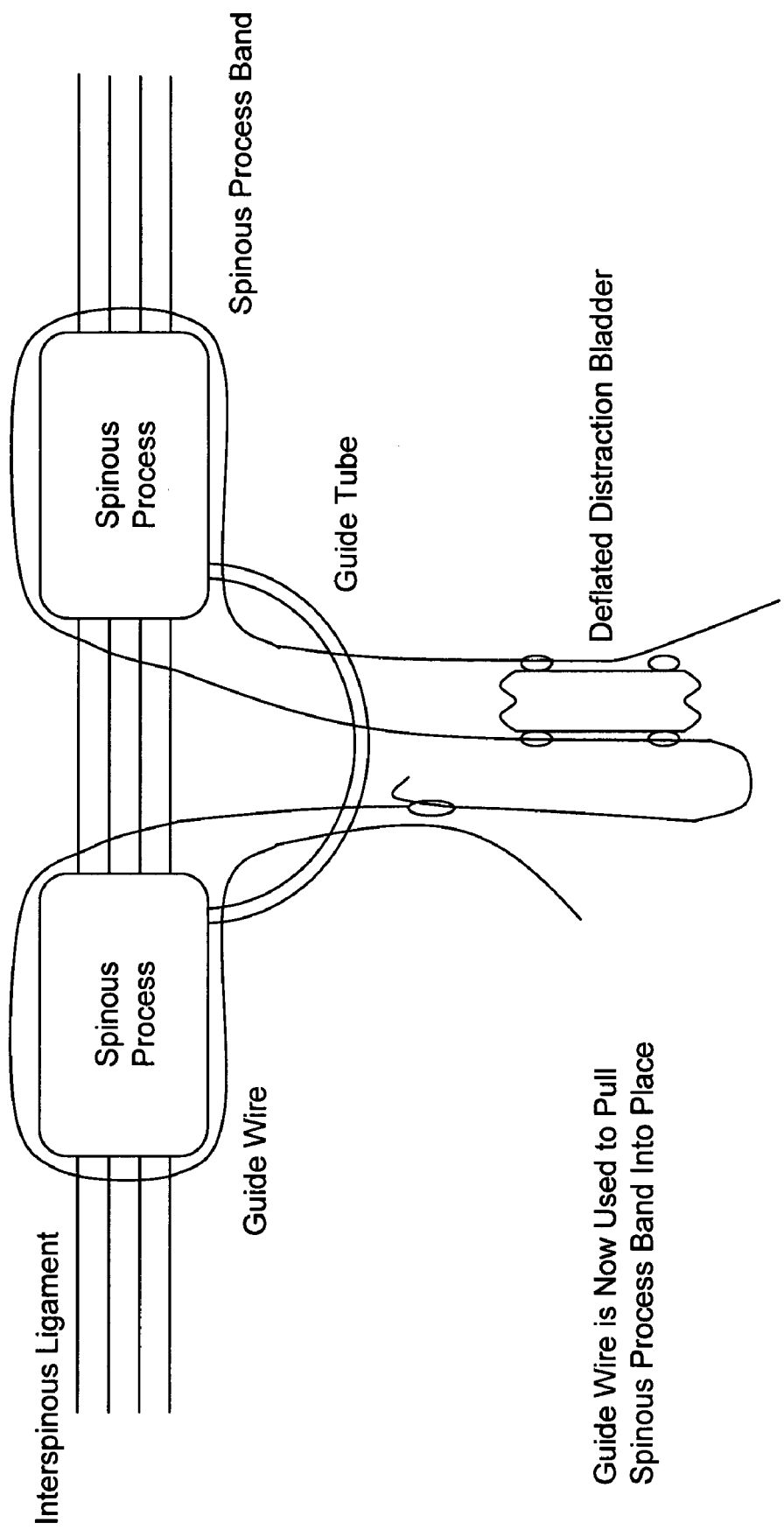
FIG. 16 is a planar view illustrating a still further aspect/step of the interspinous distraction system and the associated minimally-invasive method of insertion of FIGS. 12-15.
Figure 17:
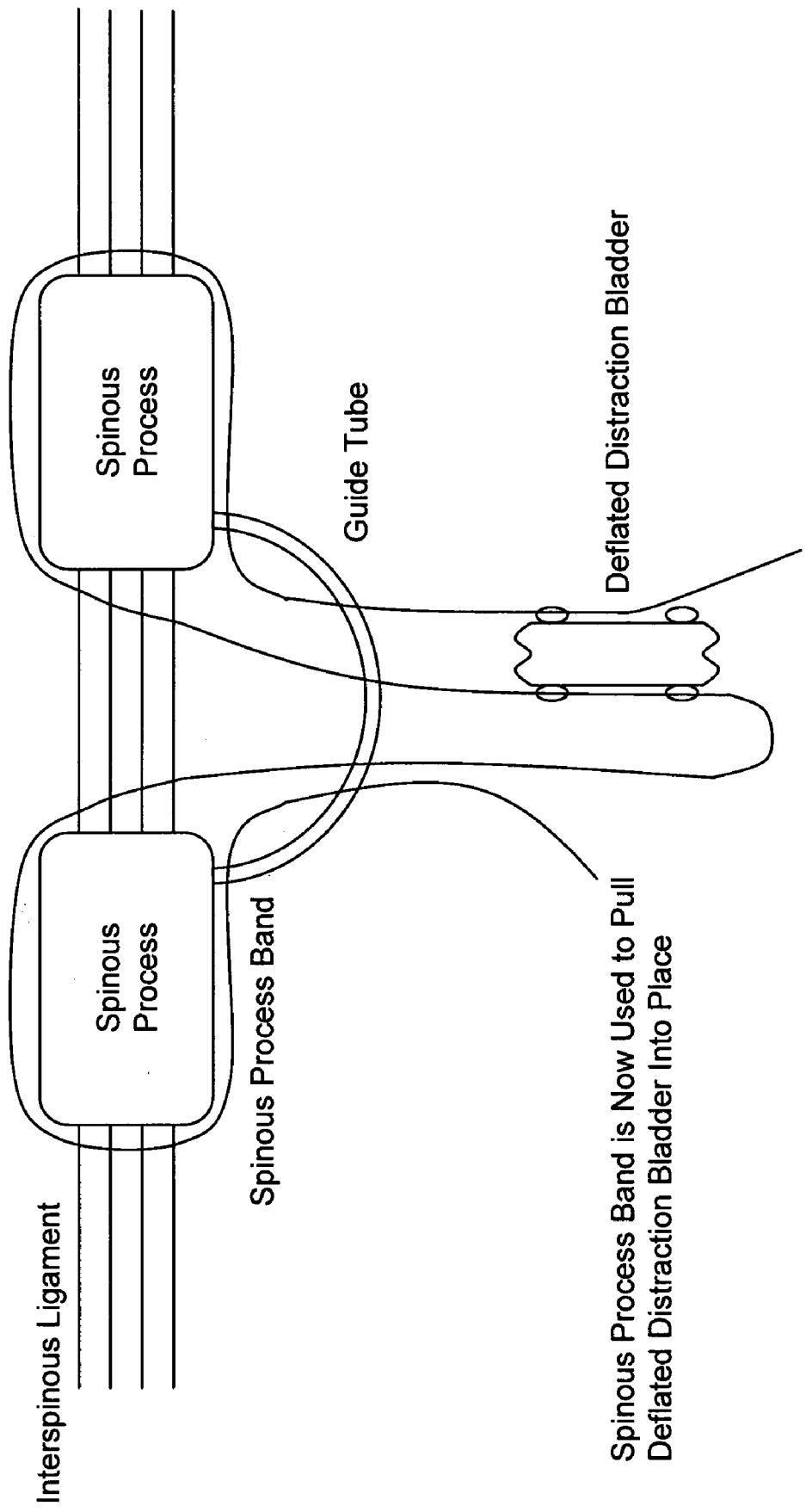
FIG. 17 is a planar view illustrating a still further aspect/step of the interspinous distraction system and the associated minimally-invasive method of insertion of FIGS. 12-16.
Figure 18:
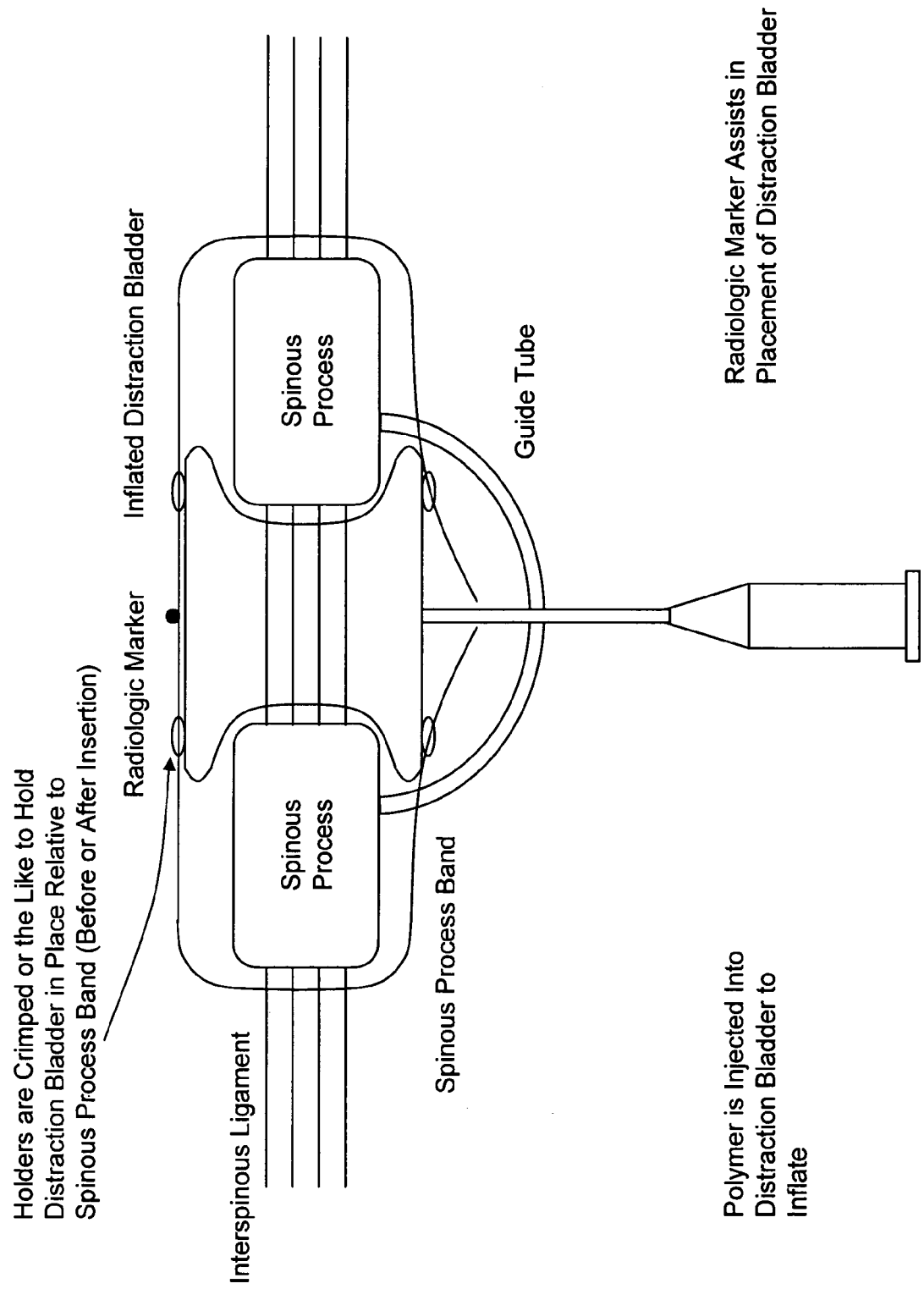
FIG. 18 is a planar view illustrating a still further aspect/step of the interspinous distraction system and the associated minimally-invasive method of insertion of FIGS. 12-17.
Figure 19:
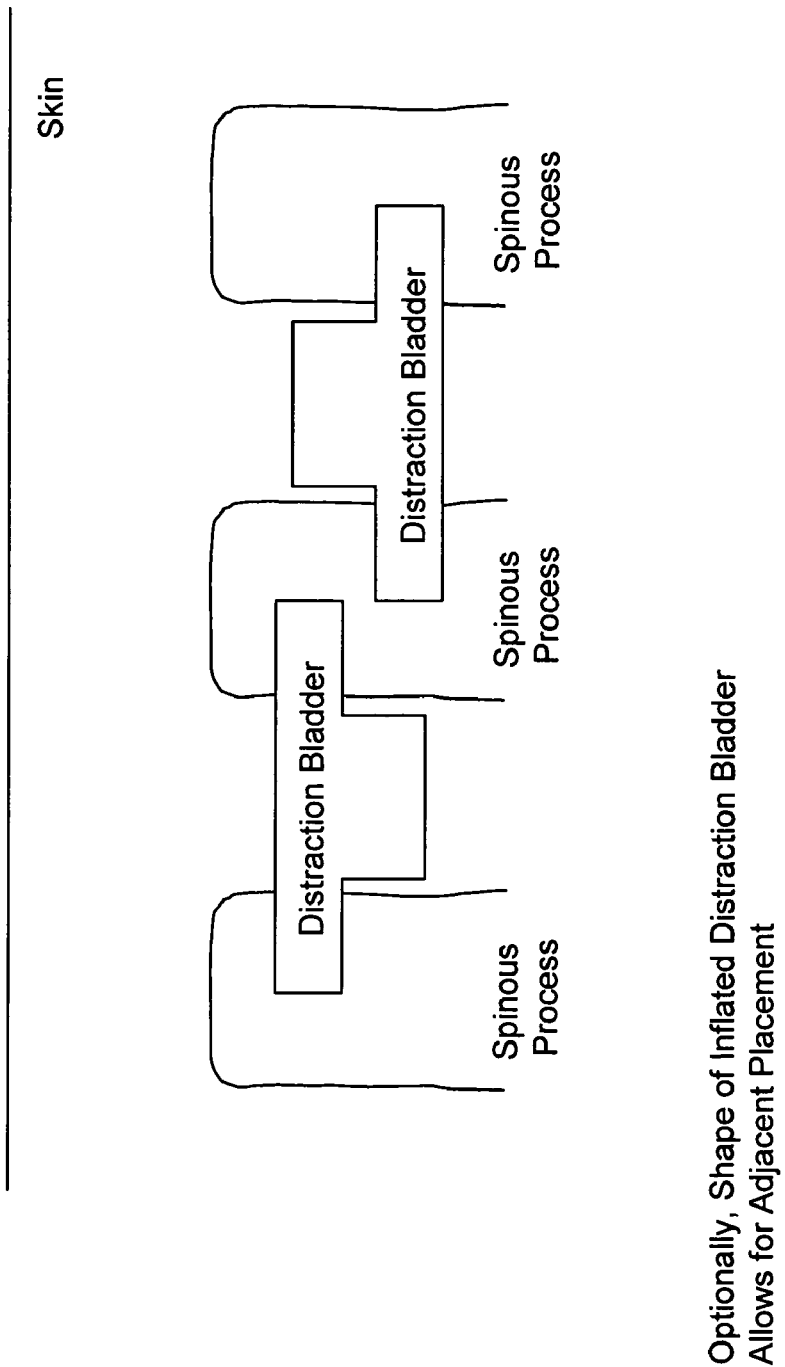
FIG. 19 is a planar view illustrating an alternative embodiment of the interspinous distraction system of FIGS. 12-18.
Figure 20:
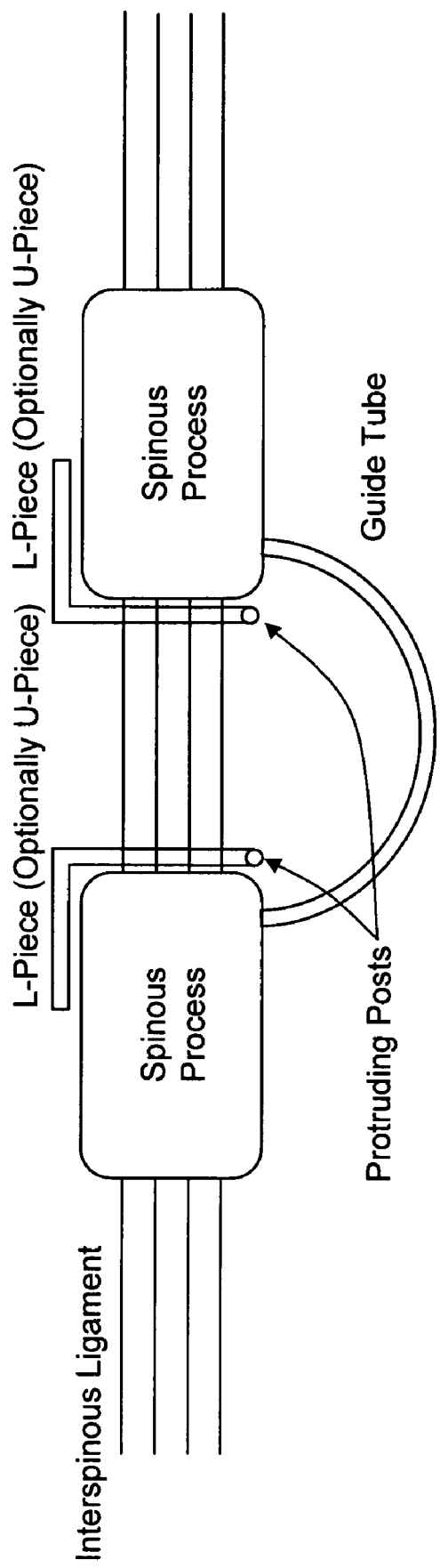
FIG. 20 is a planar view illustrating one aspect/step of another alternative embodiment of an interspinous distraction system and an associated method of insertion, the interspinous distraction system utilizing a polymer-filled packet and a plurality of L or U-shaped members.
Figure 21:
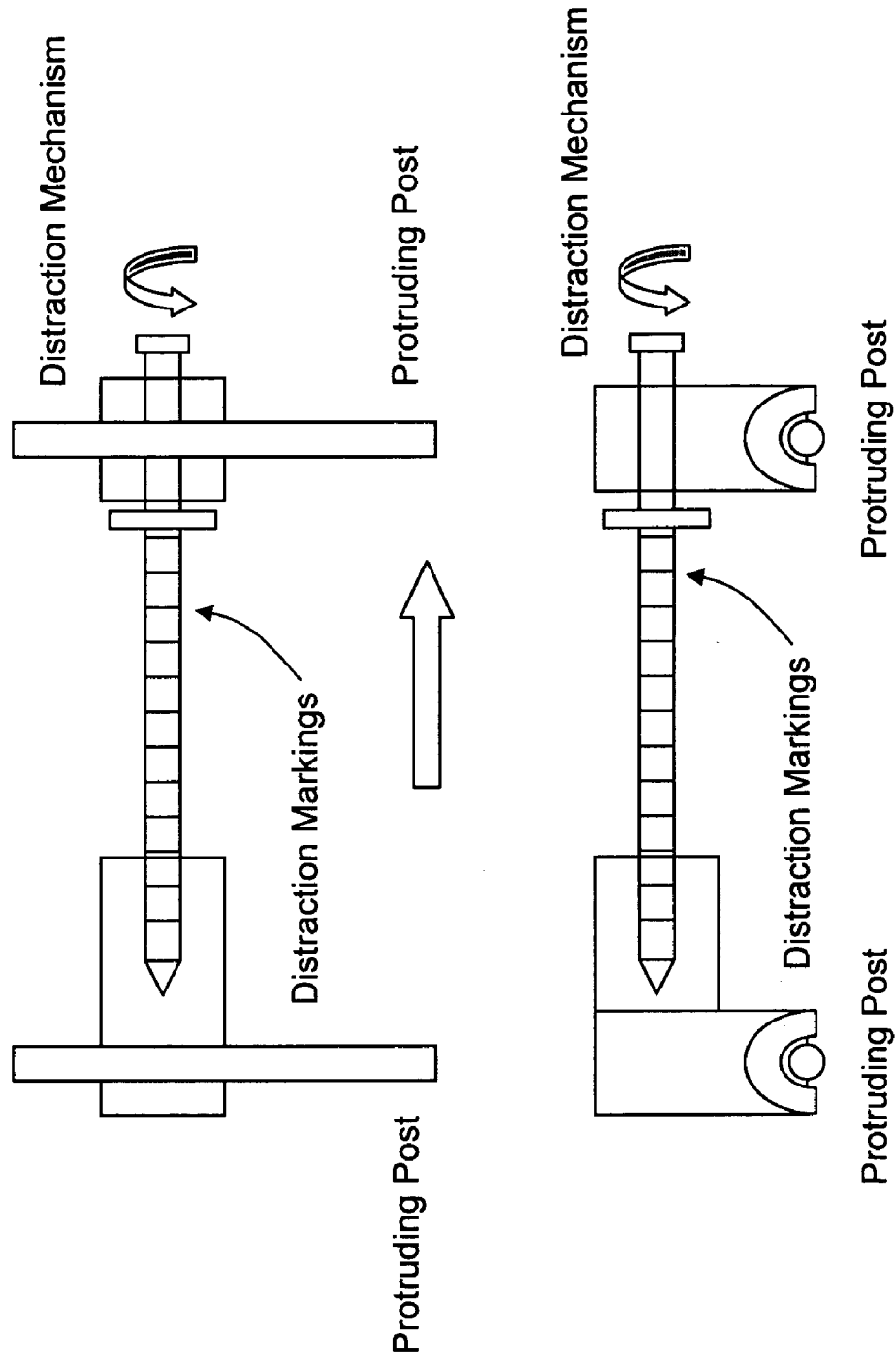
FIG. 21 is a planar view illustrating another aspect/step of the interspinous distraction system and the associated method of insertion of FIG. 20.
Figure 22:
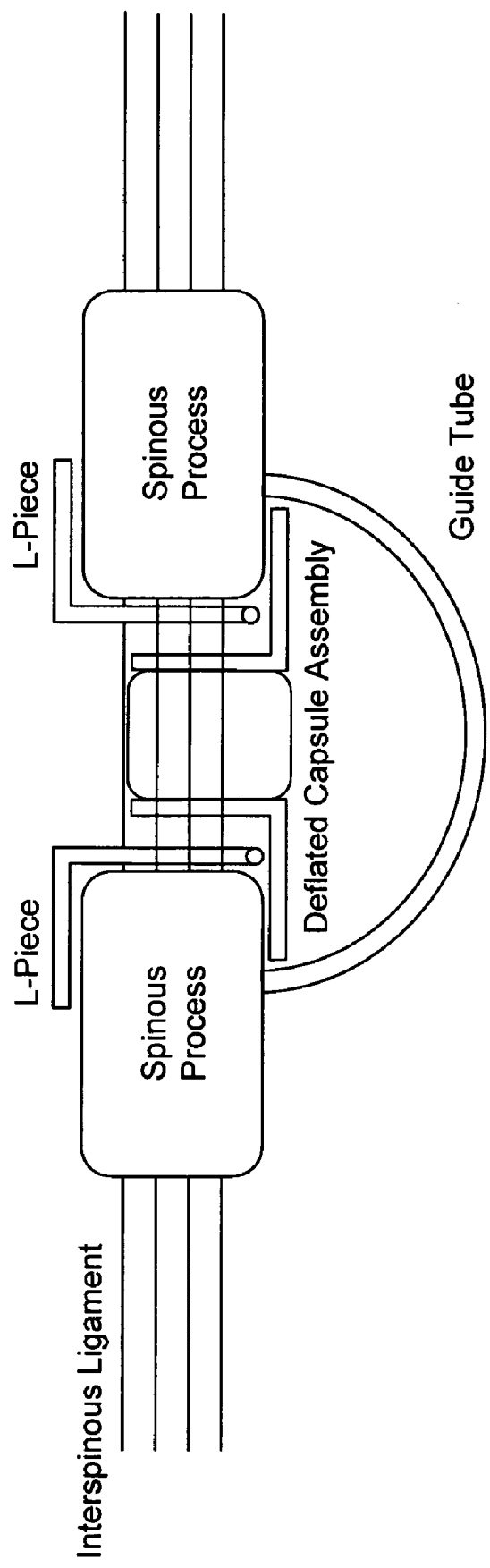
FIG. 22 is a planar view illustrating a further aspect/step of the interspinous distraction system and the associated method of insertion of FIGS. 20 and 21.
Figure 23:
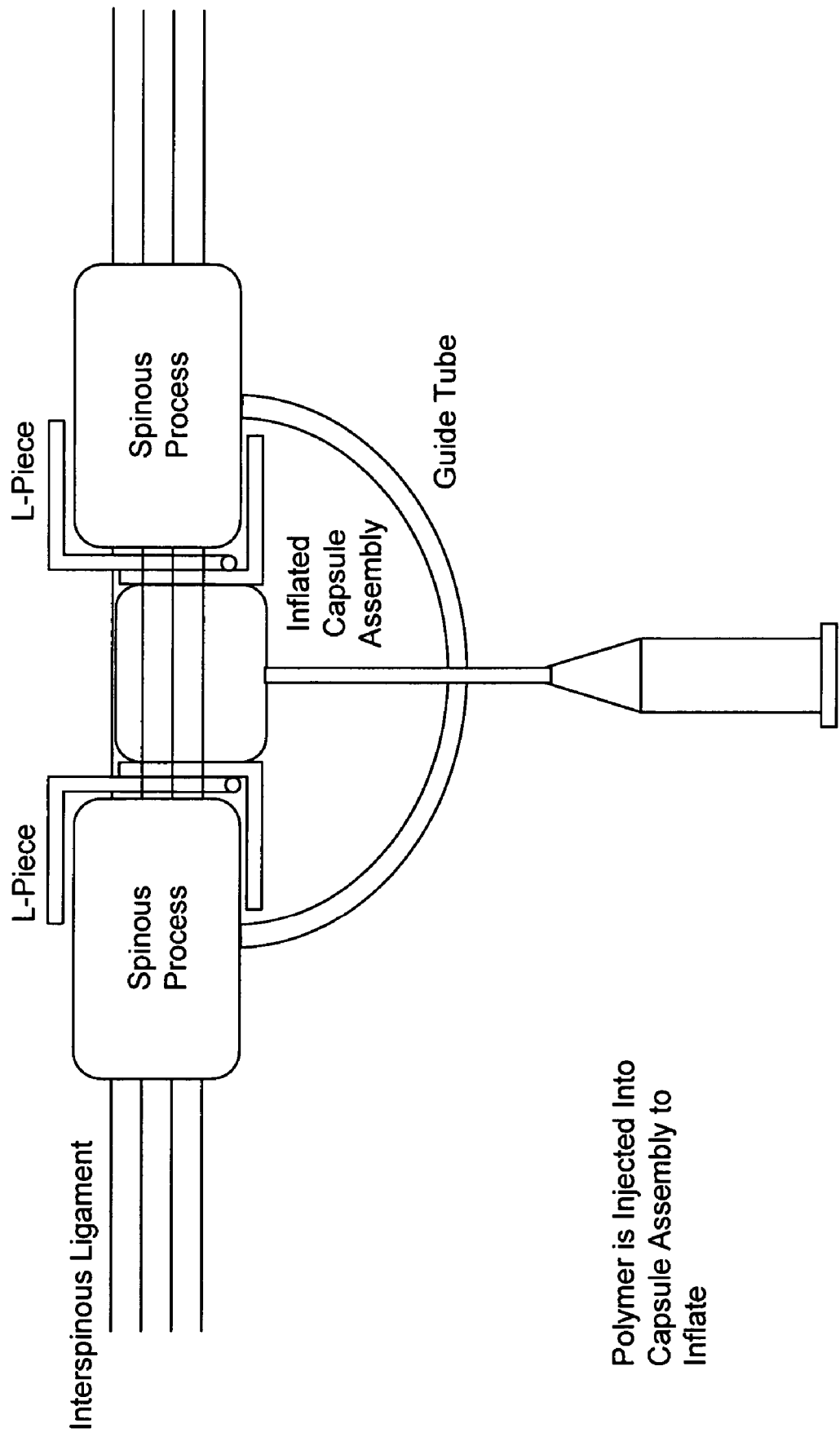
FIG. 23 is a planar view illustrating a still further aspect/step of the interspinous distraction system and the associated method of insertion of FIGS. 20-22.
Figure 24:
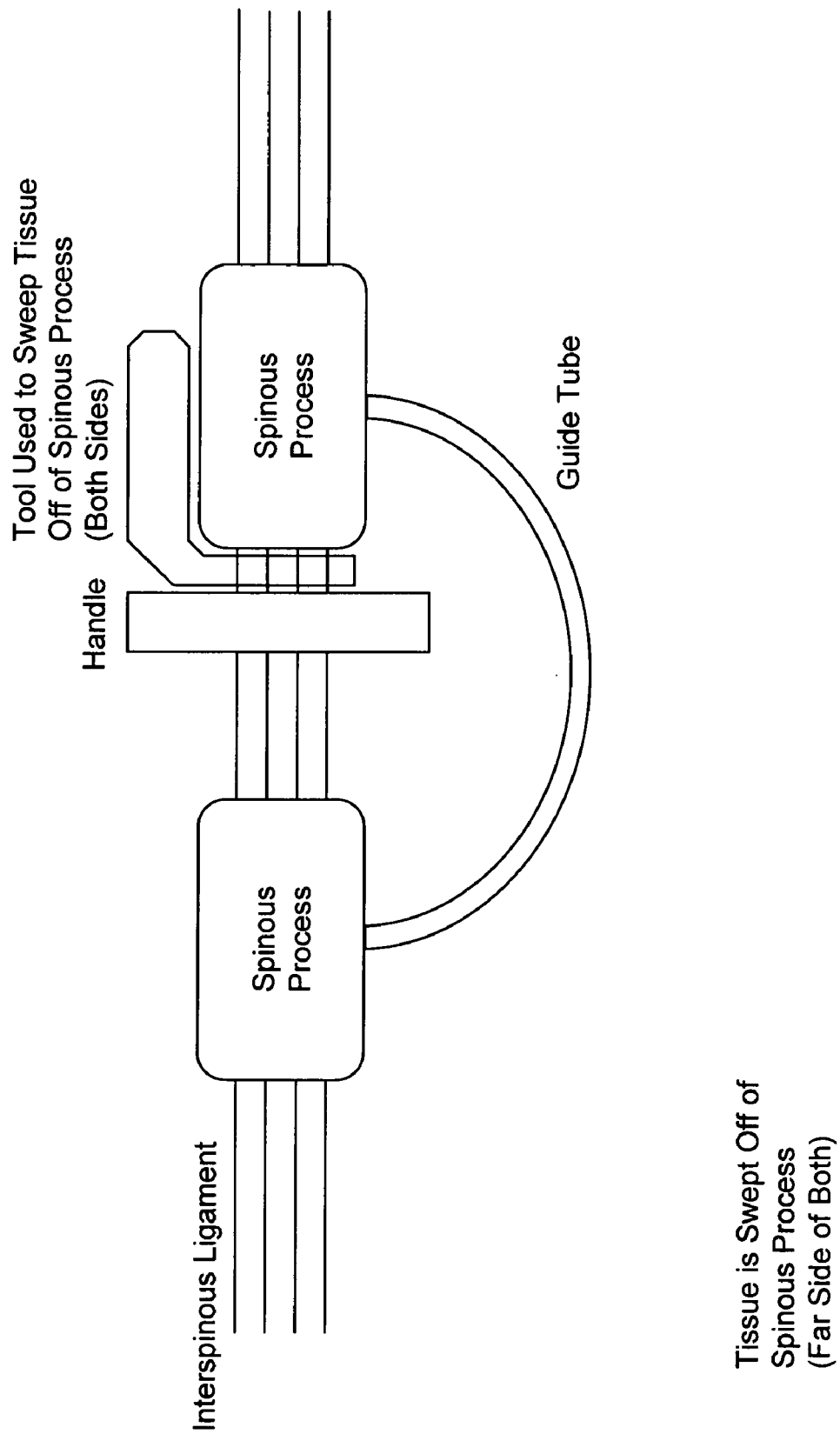
FIG. 24 is a planar view illustrating one aspect/step of a further alternative embodiment of an interspinous distraction system and an associated method of insertion, the interspinous distraction system utilizing a polymer-filled packet, one or more lines, and one or more line guides.
Figure 25:
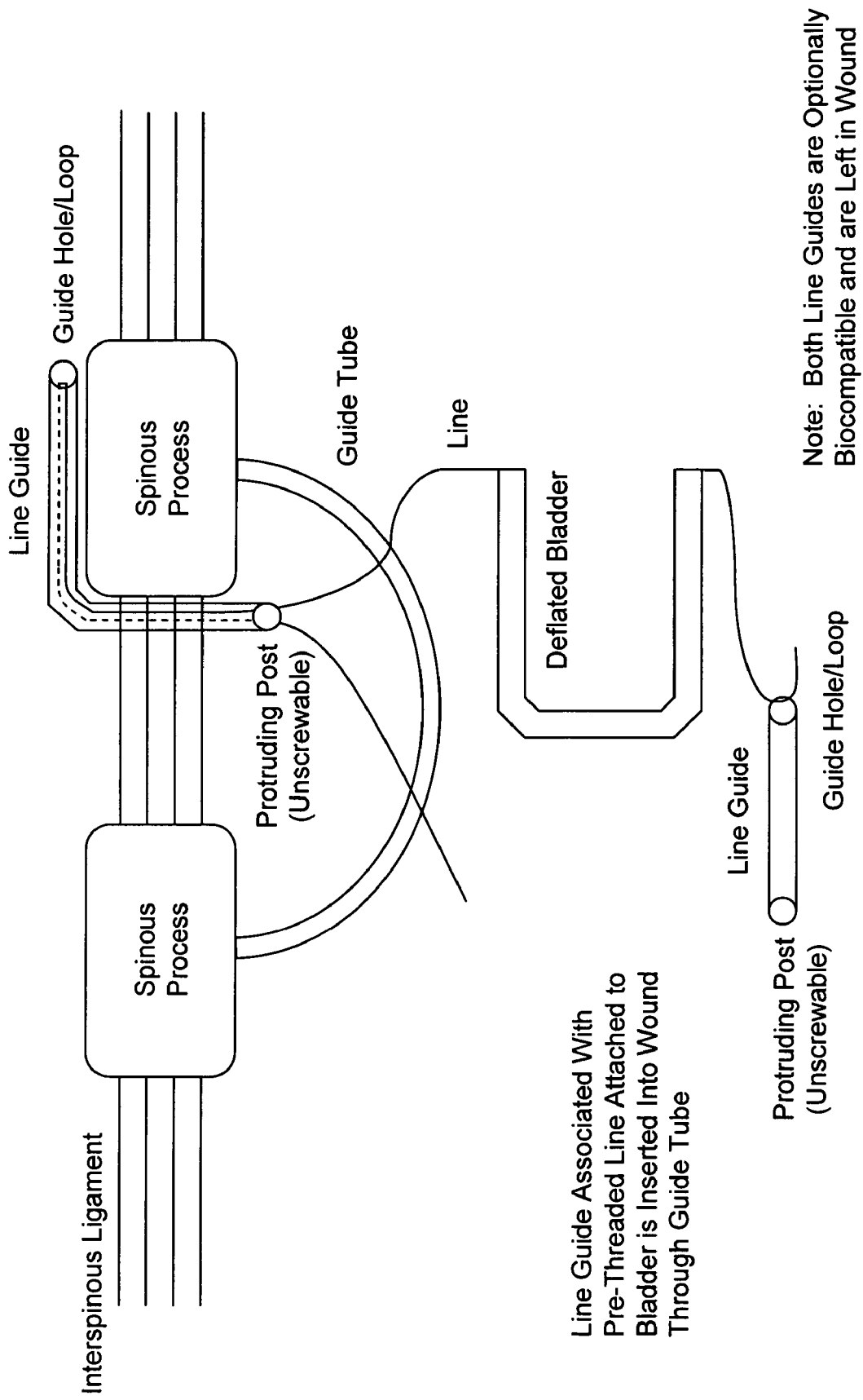
FIG. 25 is a planar view illustrating another aspect/step of the interspinous distraction system and the associated method of insertion of FIG. 24.
Figure 26:
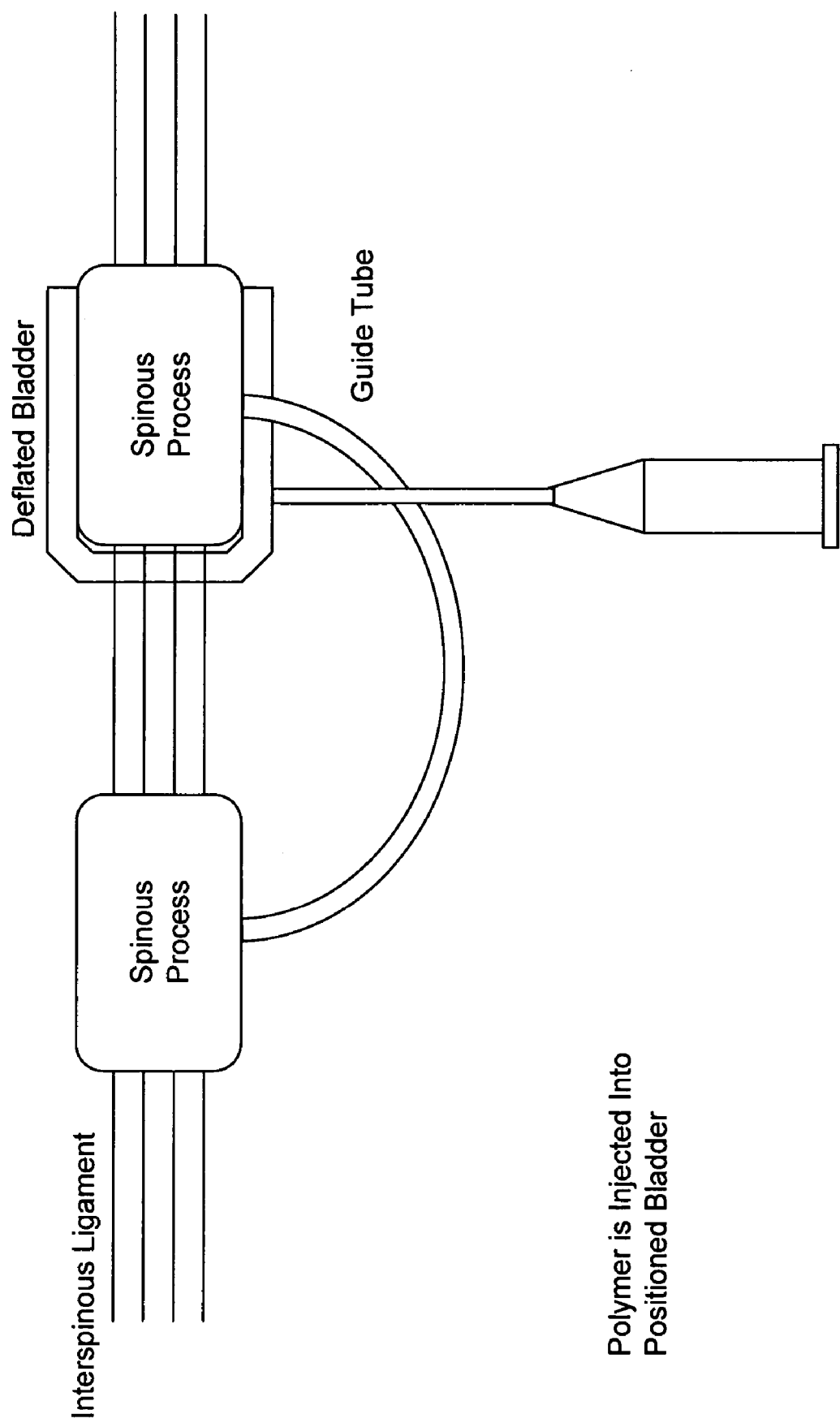
FIG. 26 is a planar view illustrating a further aspect/step of the interspinous distraction system and the associated method of insertion of FIGS. 24 and 25.
Figure 27:
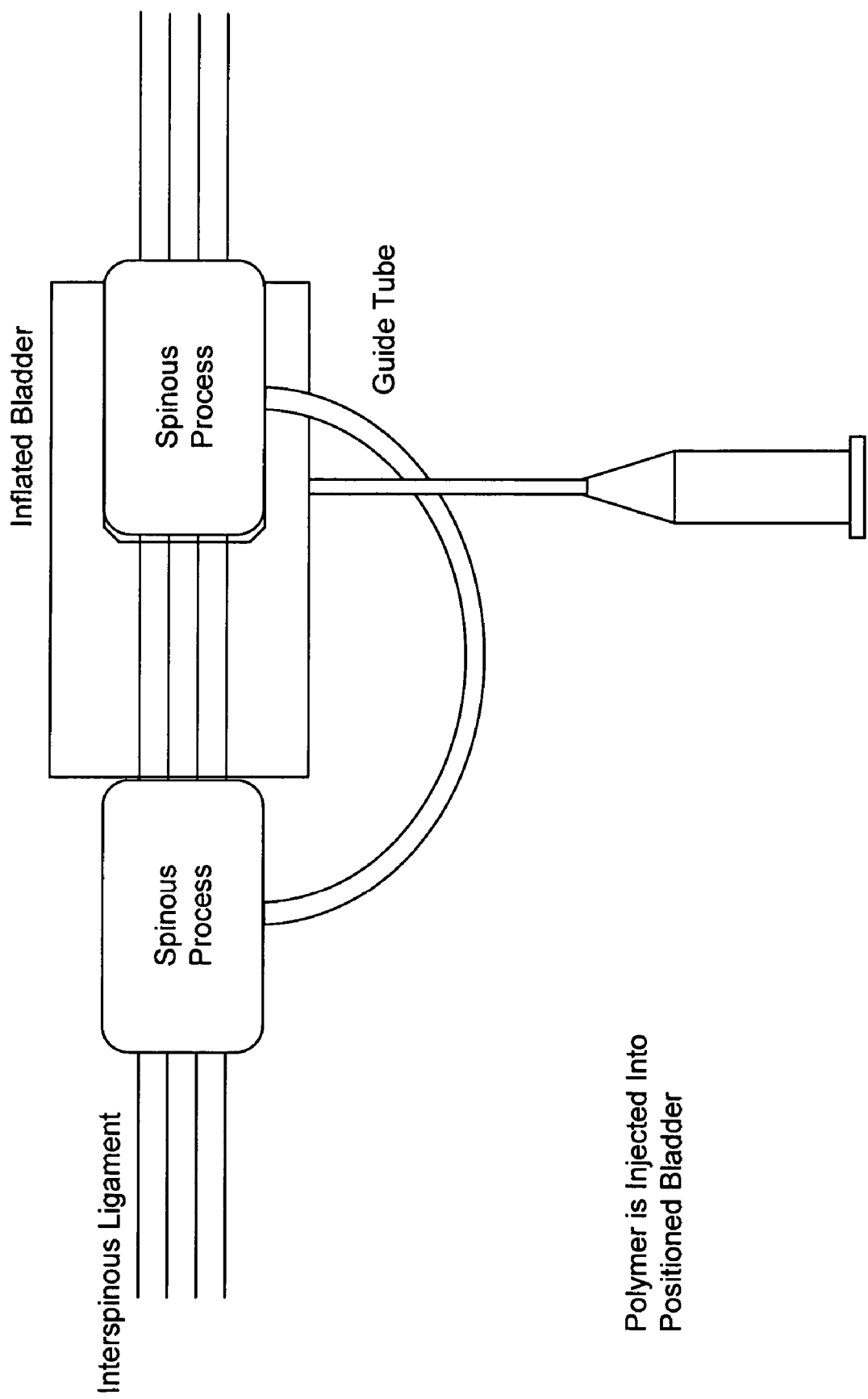
FIG. 27 is a planar view illustrating a still further aspect/step of the interspinous distraction system and the associated method of insertion of FIGS. 24-26.
Figure 28:
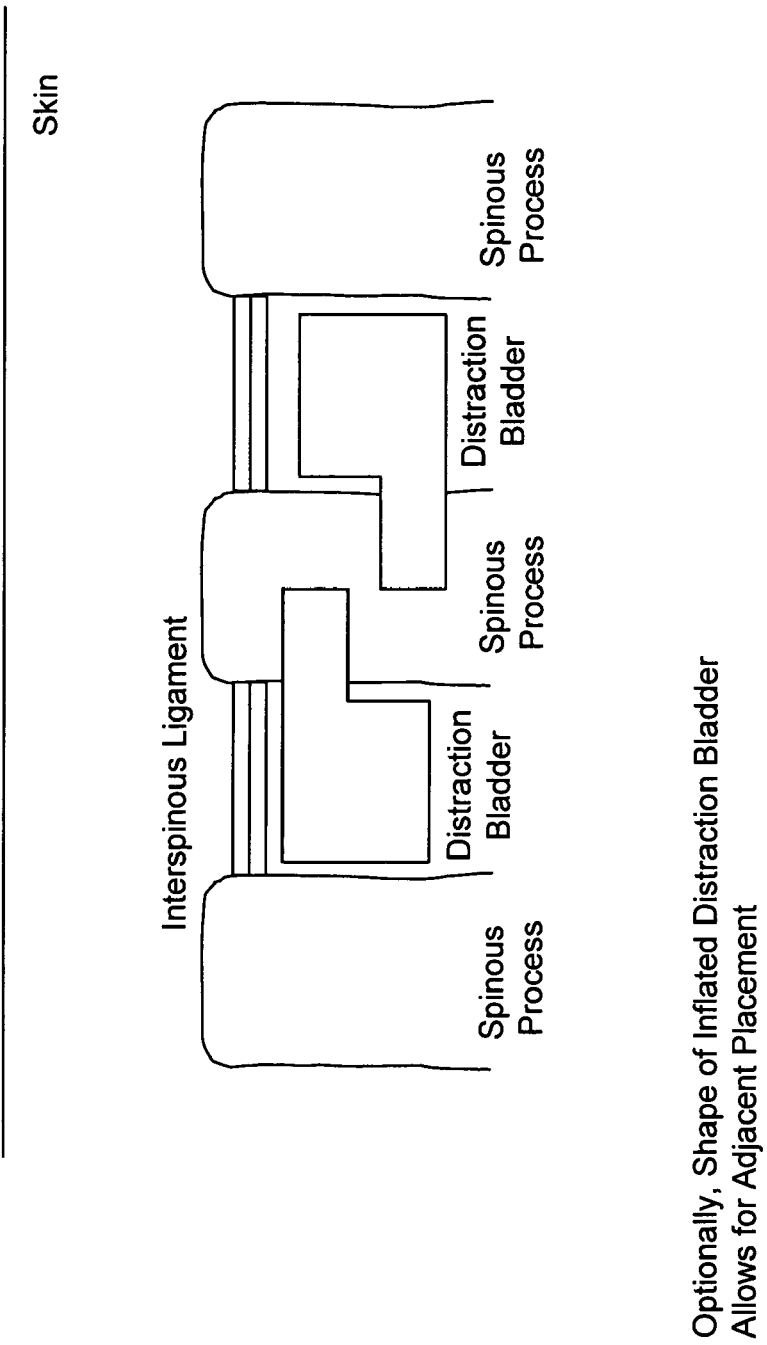
FIG. 28 is a planar view illustrating a still further aspect/step of the interspinous distraction system and the associated method of insertion of FIGS. 24-27.
Figure 29:
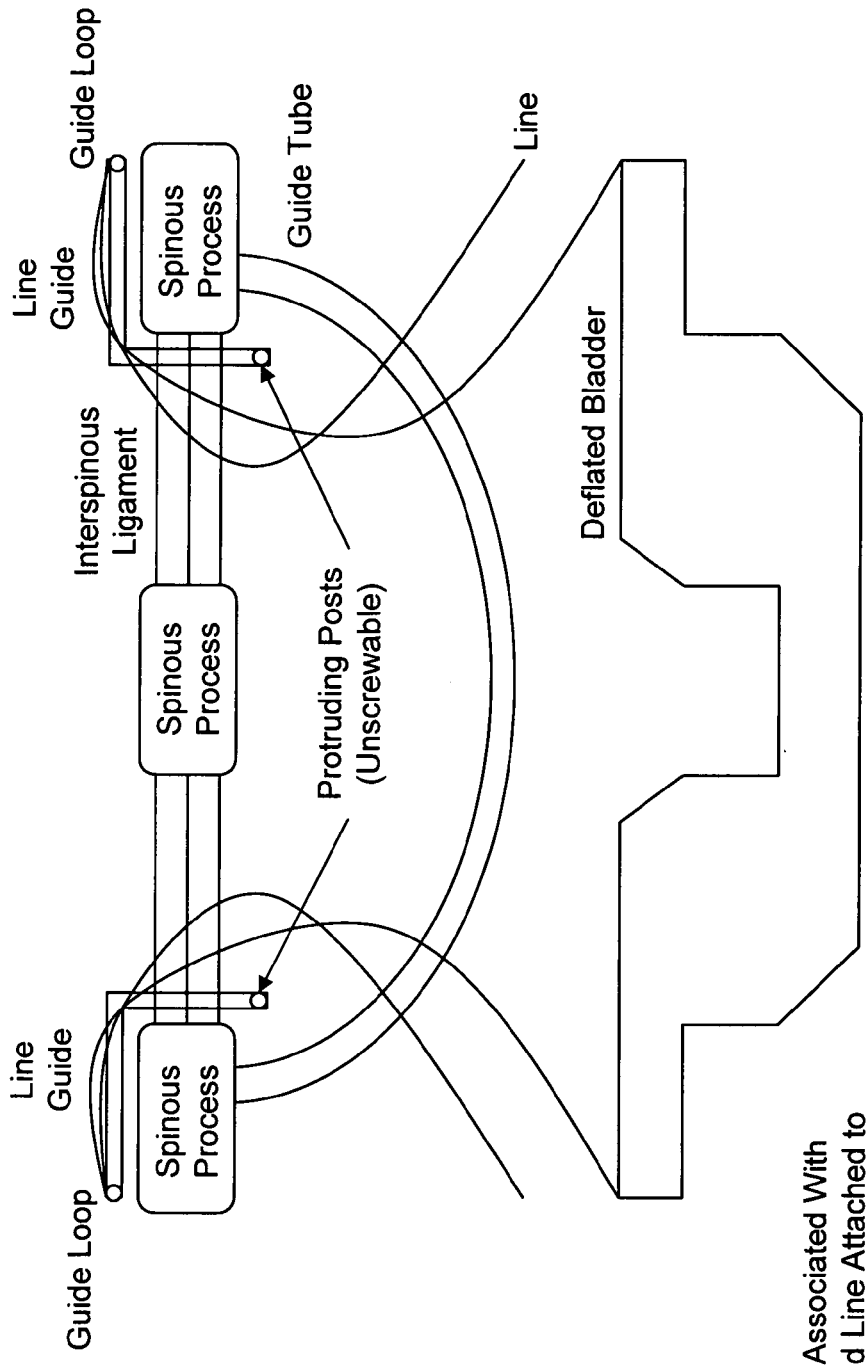
FIG. 29 is a planar view illustrating one aspect/step of a still further alternative embodiment of an interspinous distraction system and an associated method of insertion, the interspinous distraction system also utilizing a polymer-filled packet, one or more lines, and one or more line guides.
Figure 30:
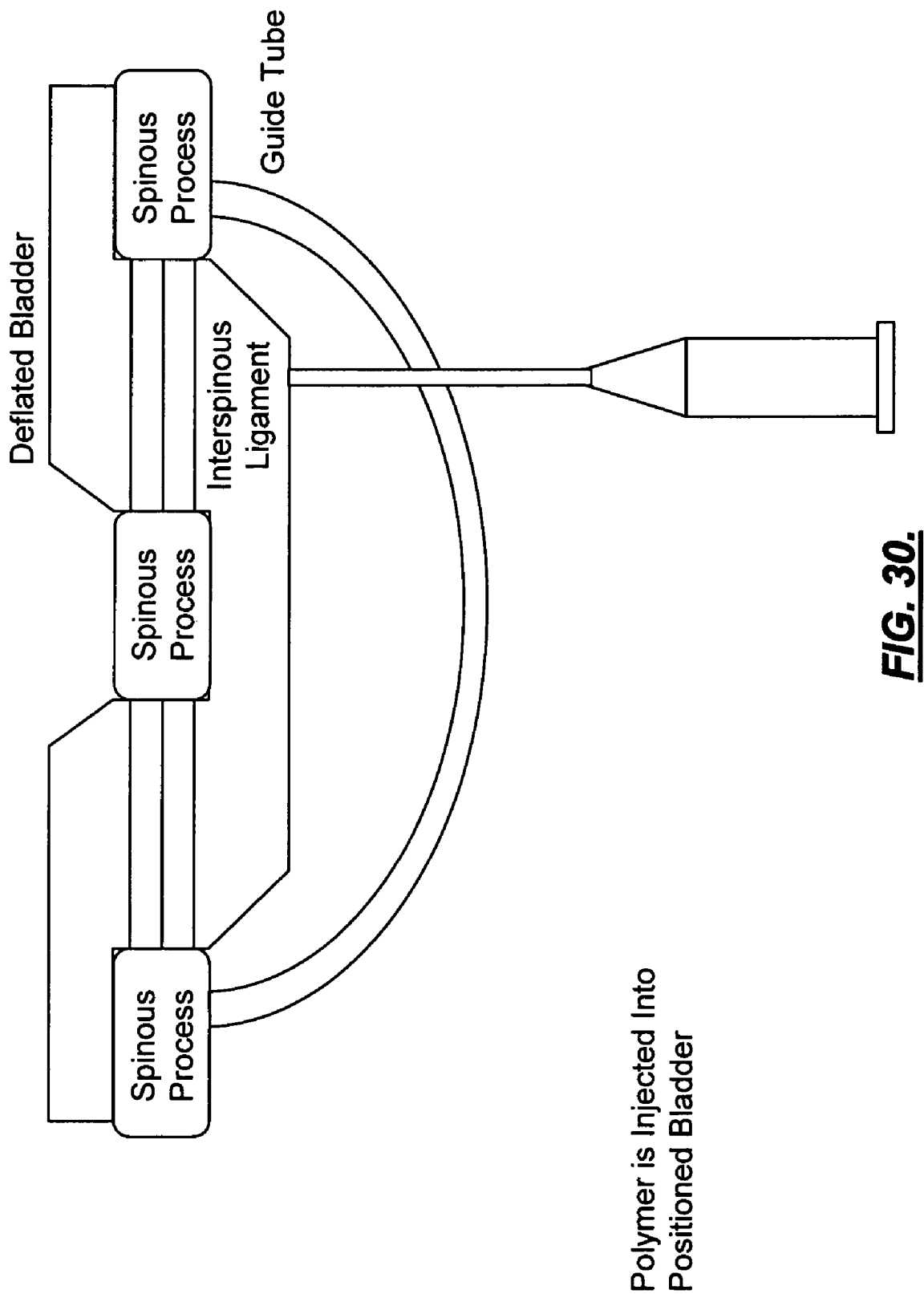
FIG. 30 is a planar view illustrating another aspect/step of the interspinous distraction system and the associated method of insertion of FIG. 29.
Figure 31:
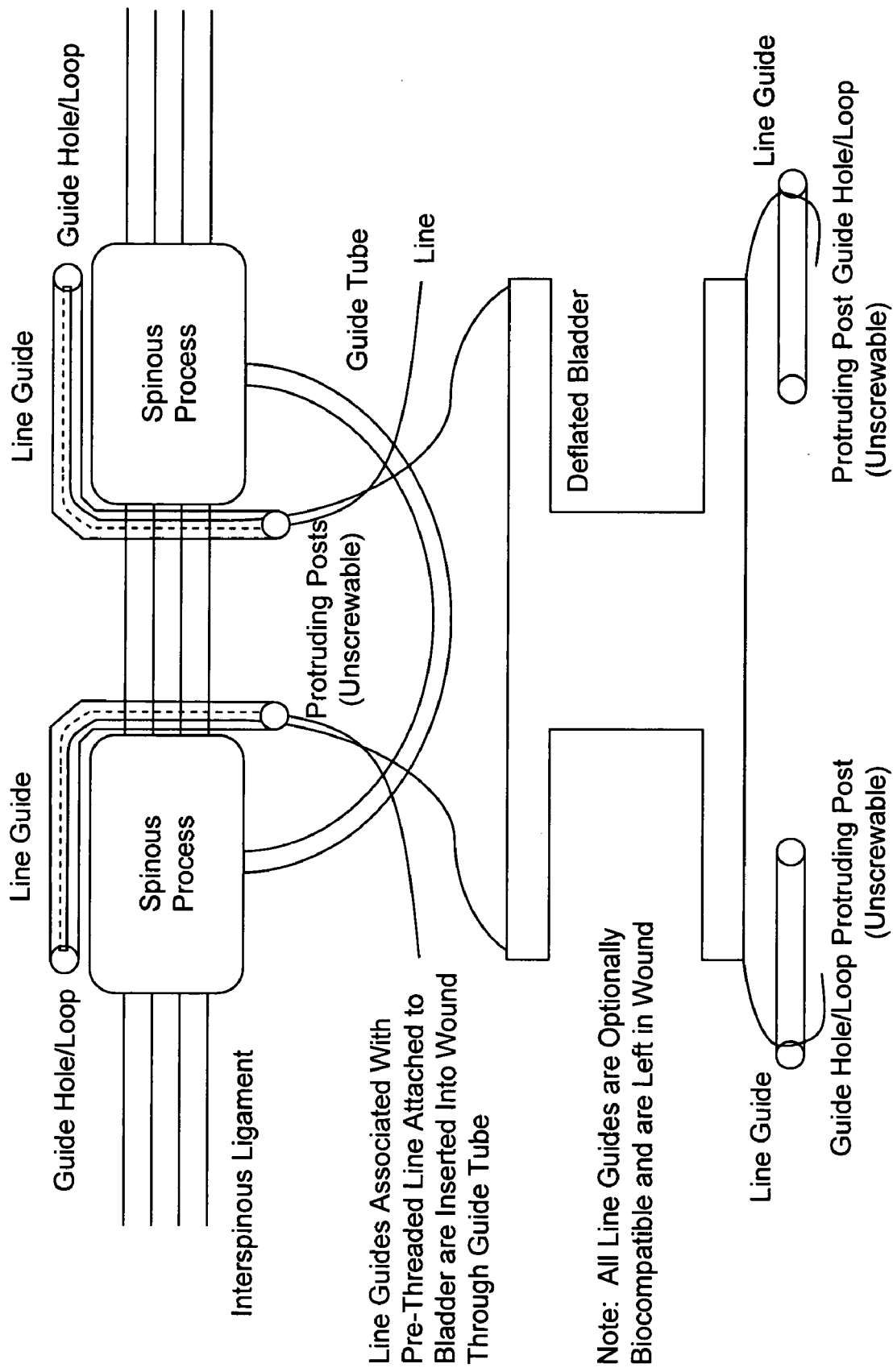
FIG. 31 is a planar view illustrating one aspect/step of a still further alternative embodiment of an interspinous distraction system and an associated method of insertion, the interspinous distraction system also utilizing a polymer-filled packet, one or more lines, and one or more line guides.
Figure 32:
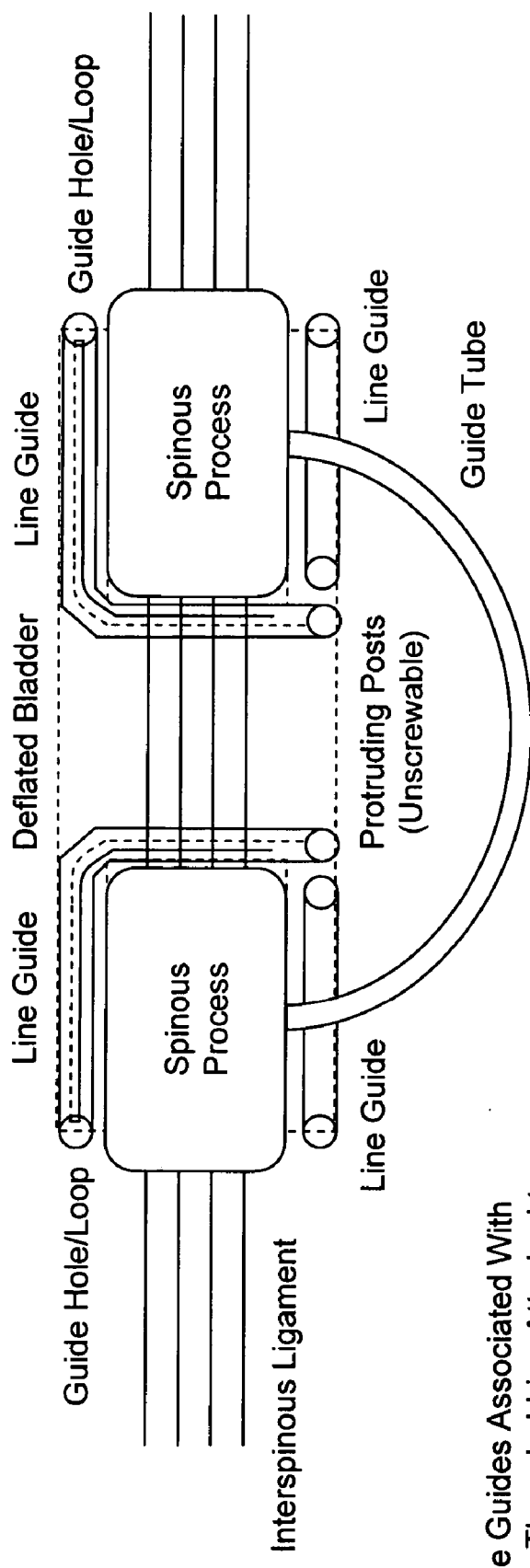
FIG. 32 is a planar view illustrating another aspect/step of the interspinous distraction system and the associated method of insertion of FIG. 31.
Figure 33:
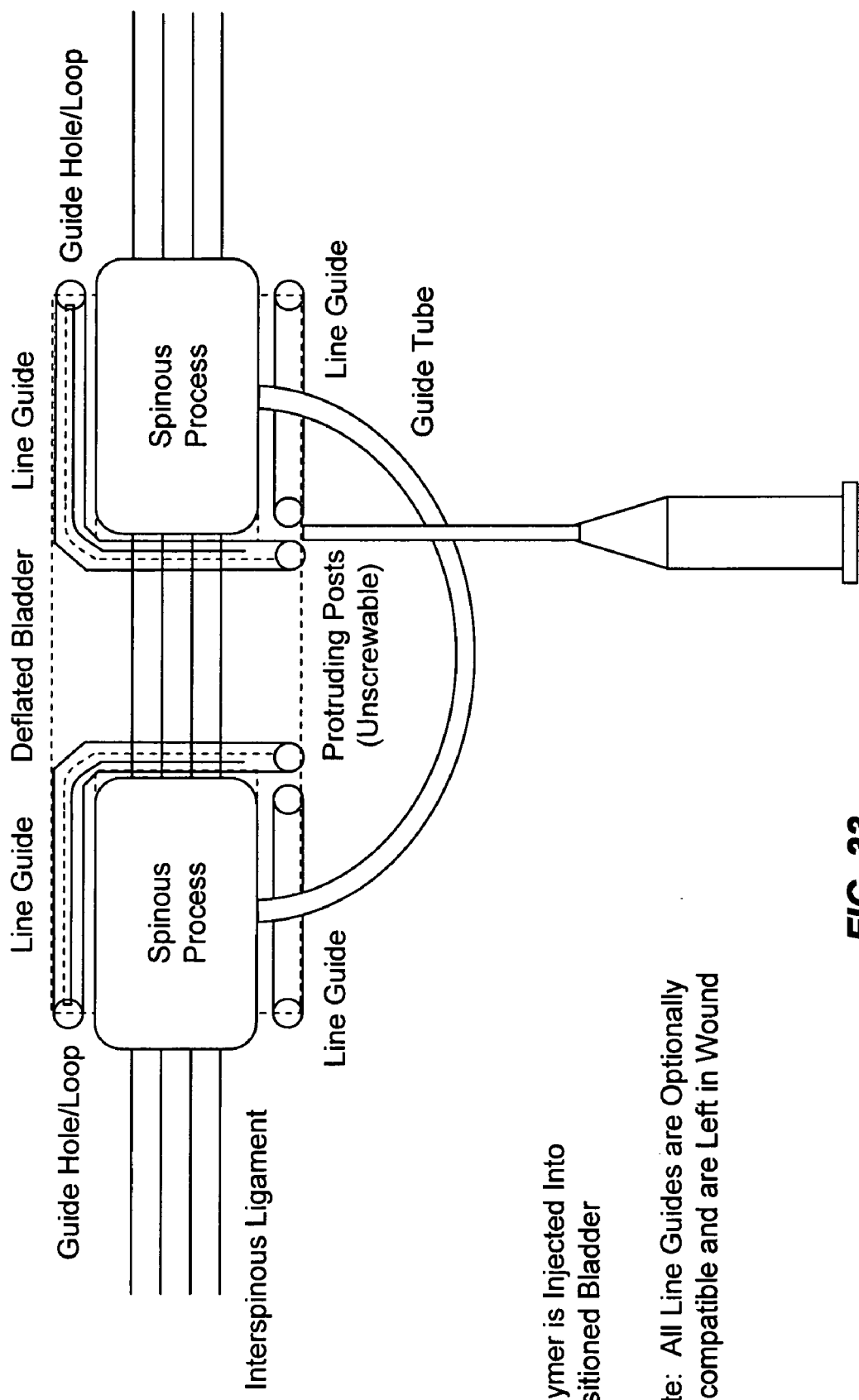
FIG. 33 is a planar view illustrating a further aspect/step of the interspinous distraction system and the associated method of insertion of FIGS. 31 and 32.
Figure 34:
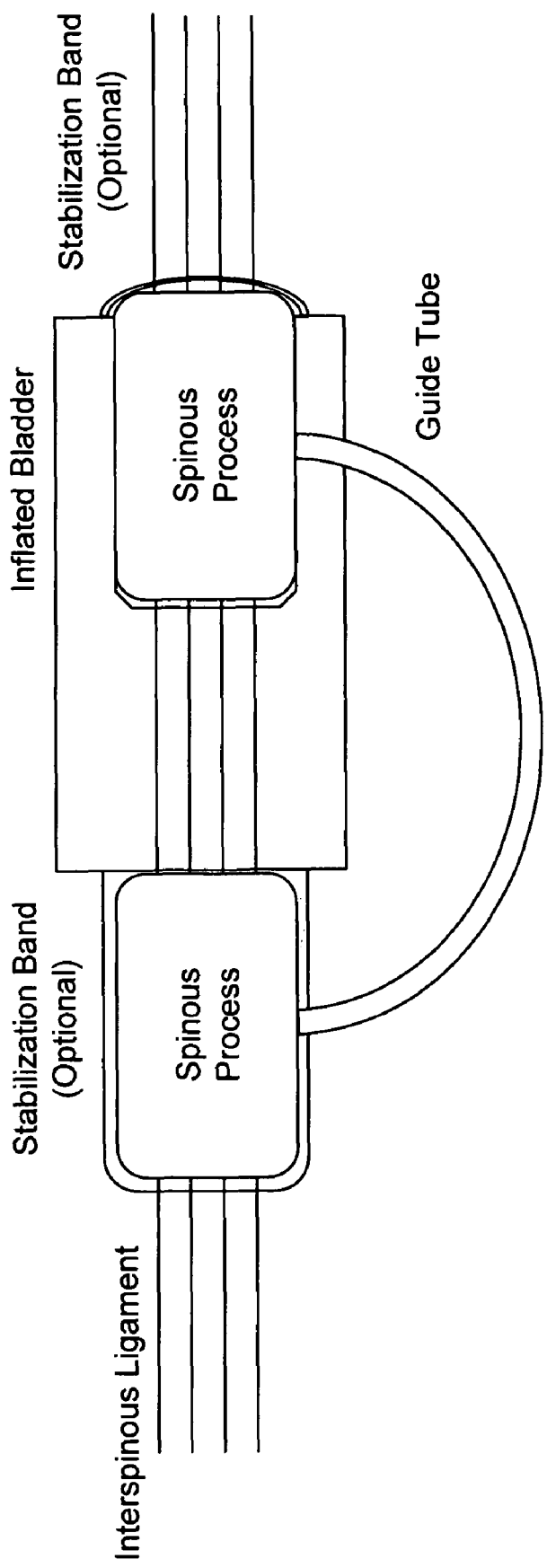
FIG. 34 is a planar view illustrating one aspect/step of a still further alternative embodiment of an interspinous distraction system and an associated method of insertion, the interspinous distraction system utilizing a polymer-filled packet and one or more stabilization bands.
Figure 35:
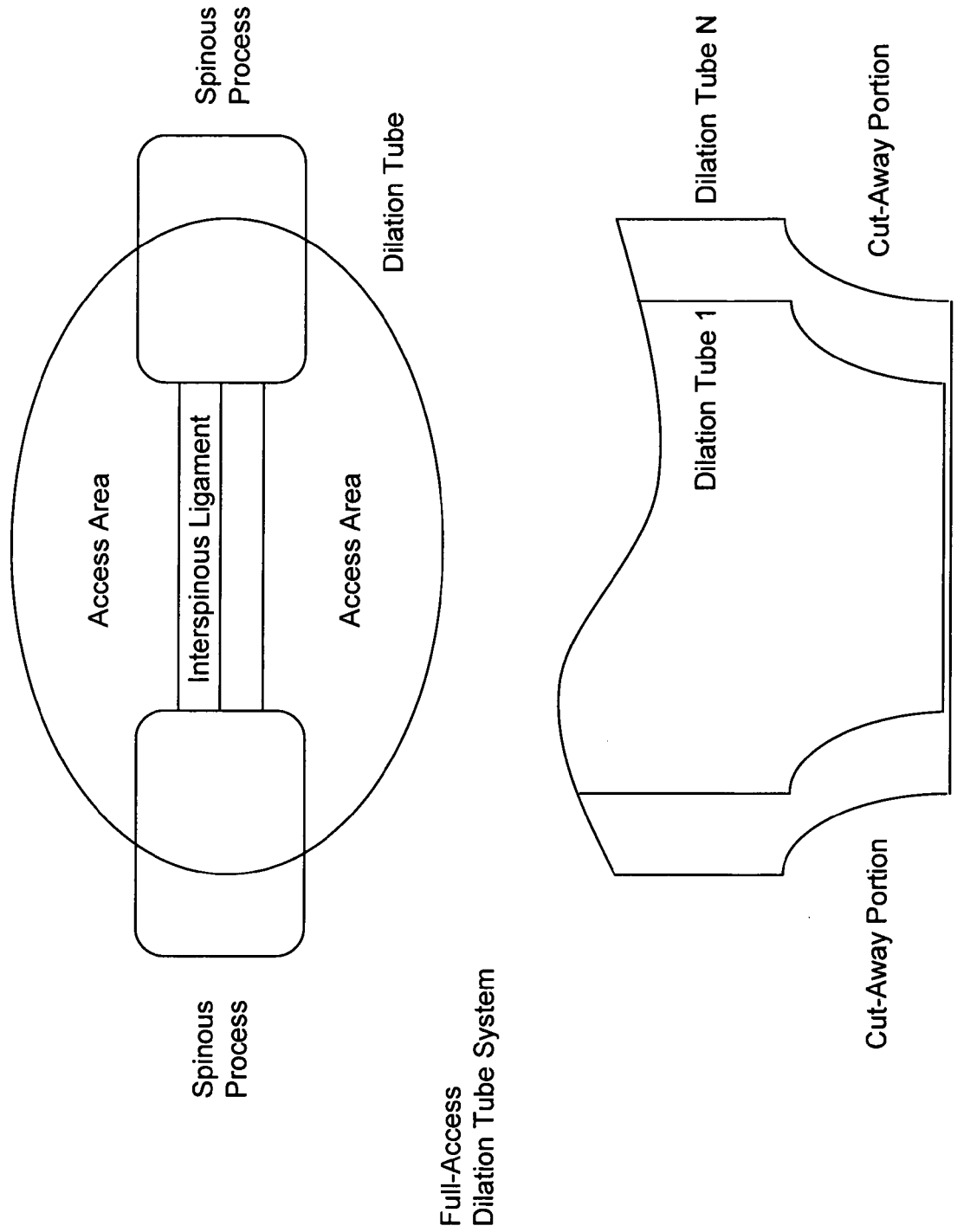
FIG. 35 is a top planar and partial cross-sectional side view of a full-access dilation tube system of the present invention.
Figure 36:
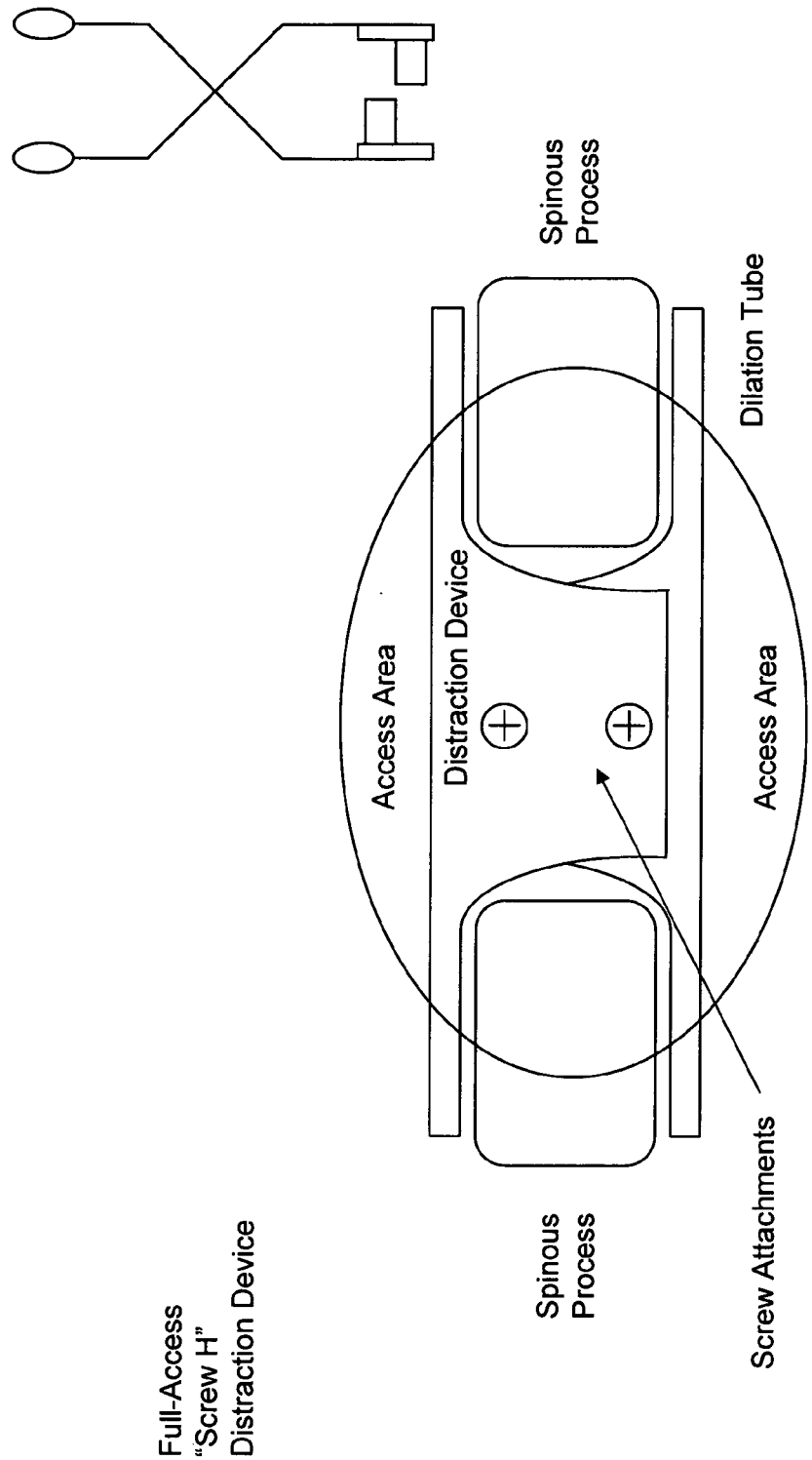
FIG. 36 is a top planar view of a full-access "screw H" distraction device of the present invention.
Figure 37:
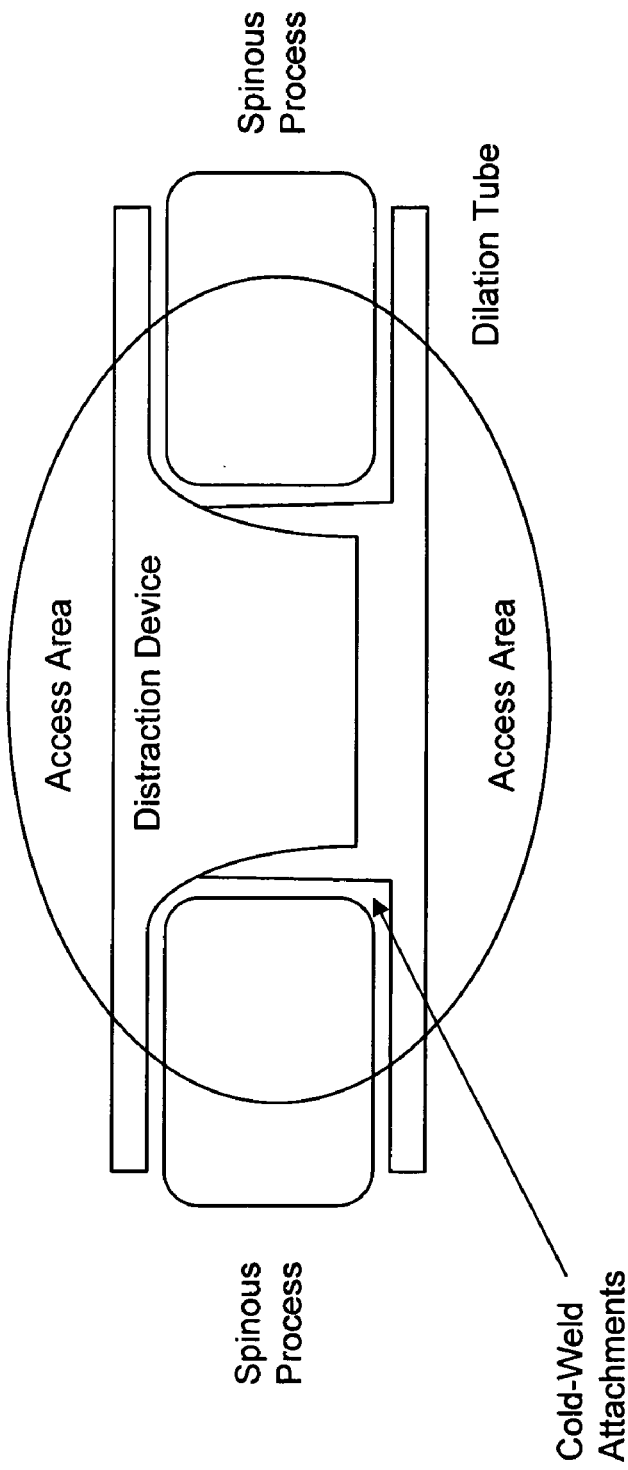
FIG. 37 is a top planar view of a full-access "cold-weld H" distraction device of the present invention.
Figure 38:
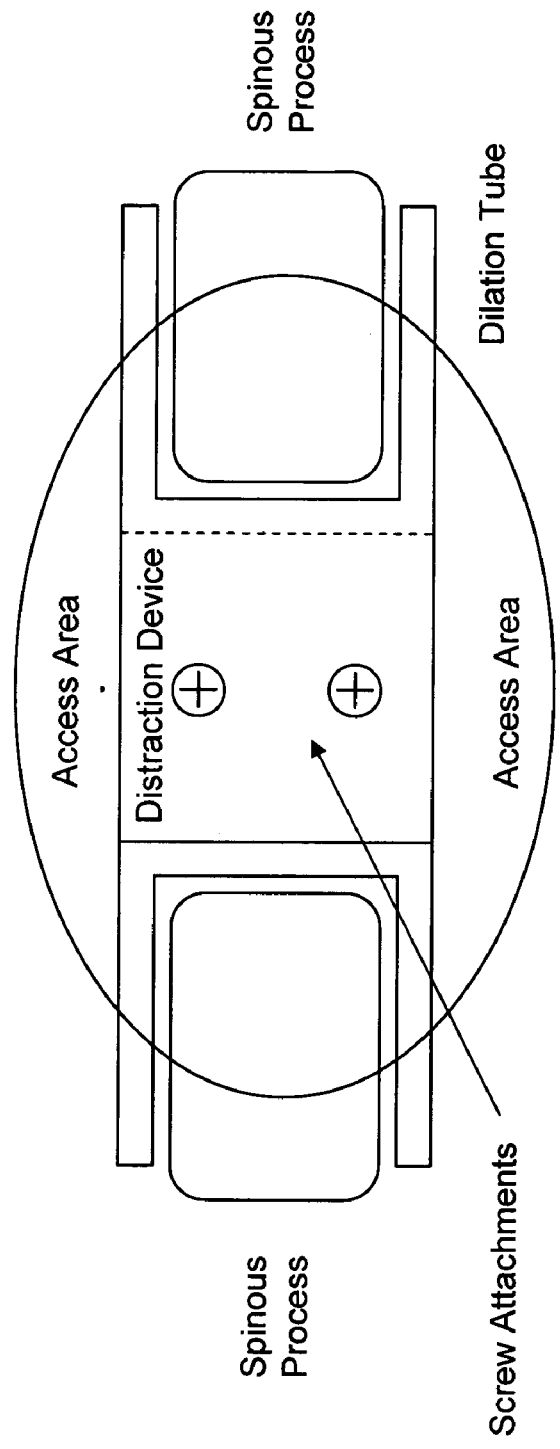
FIG. 38 is a top planar view of an alternative full-access "screw H" distraction device of the present invention.
Figure 39:
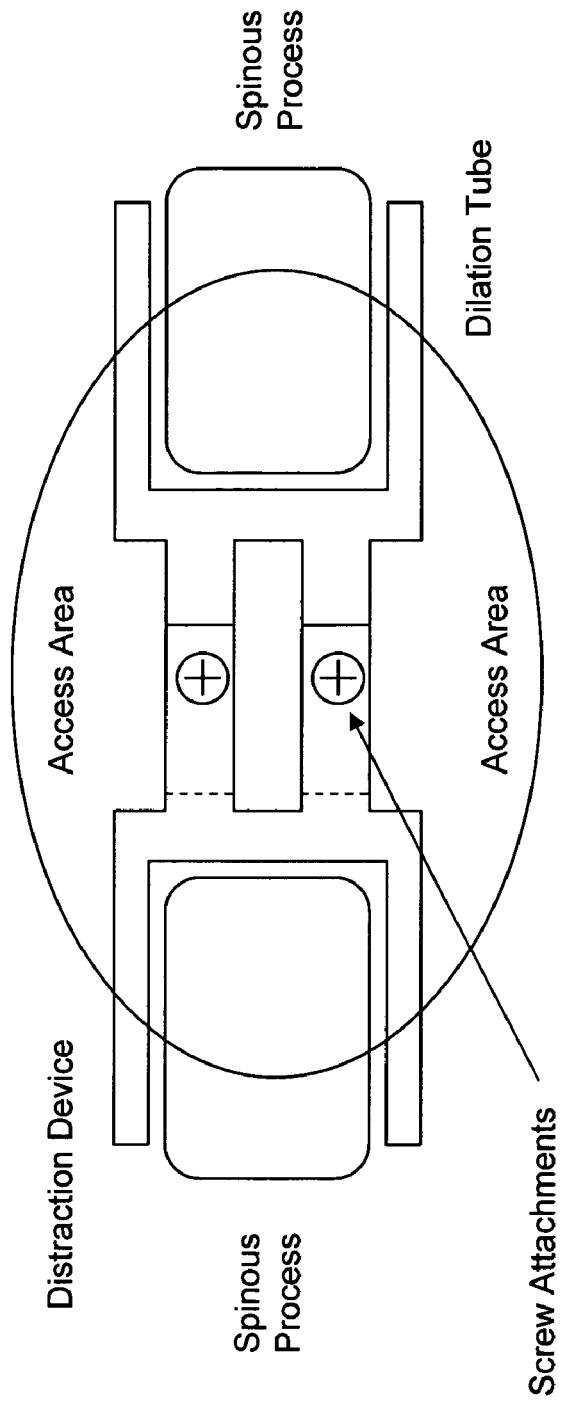
FIG. 39 is a top planar view of another alternative full-access "screw H" distraction device of the present invention.
Figure 40:
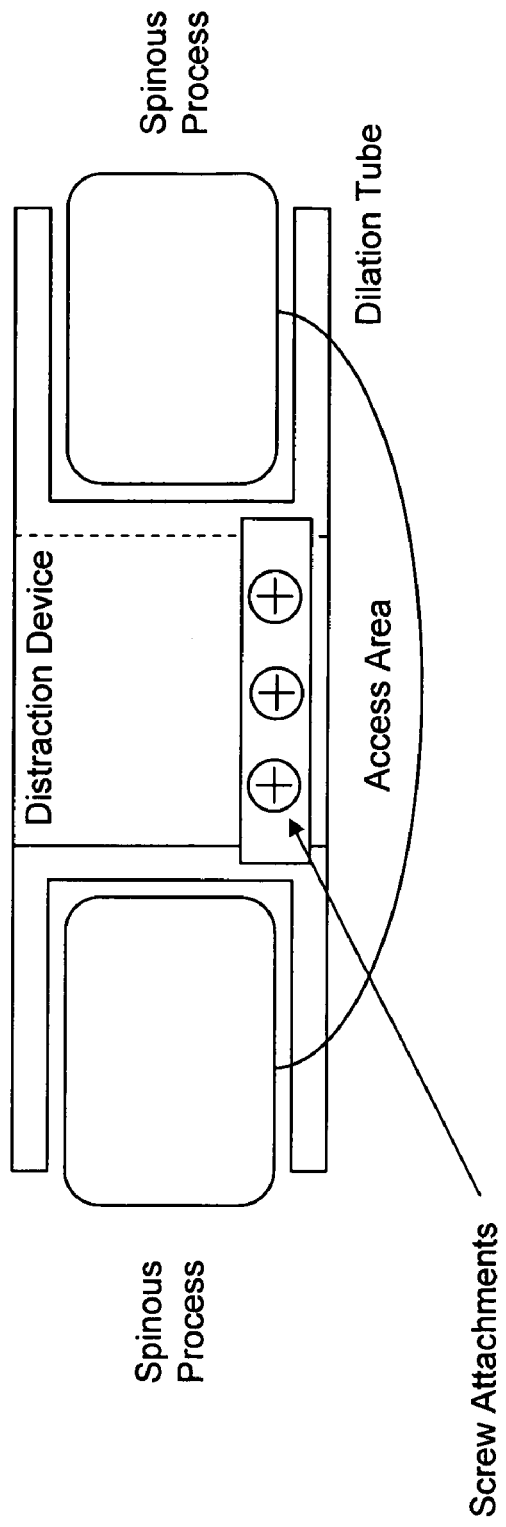
FIG. 40 is a top planar view of a partial-access "adjustable screw H" distraction device of the present invention.
Figure 42:
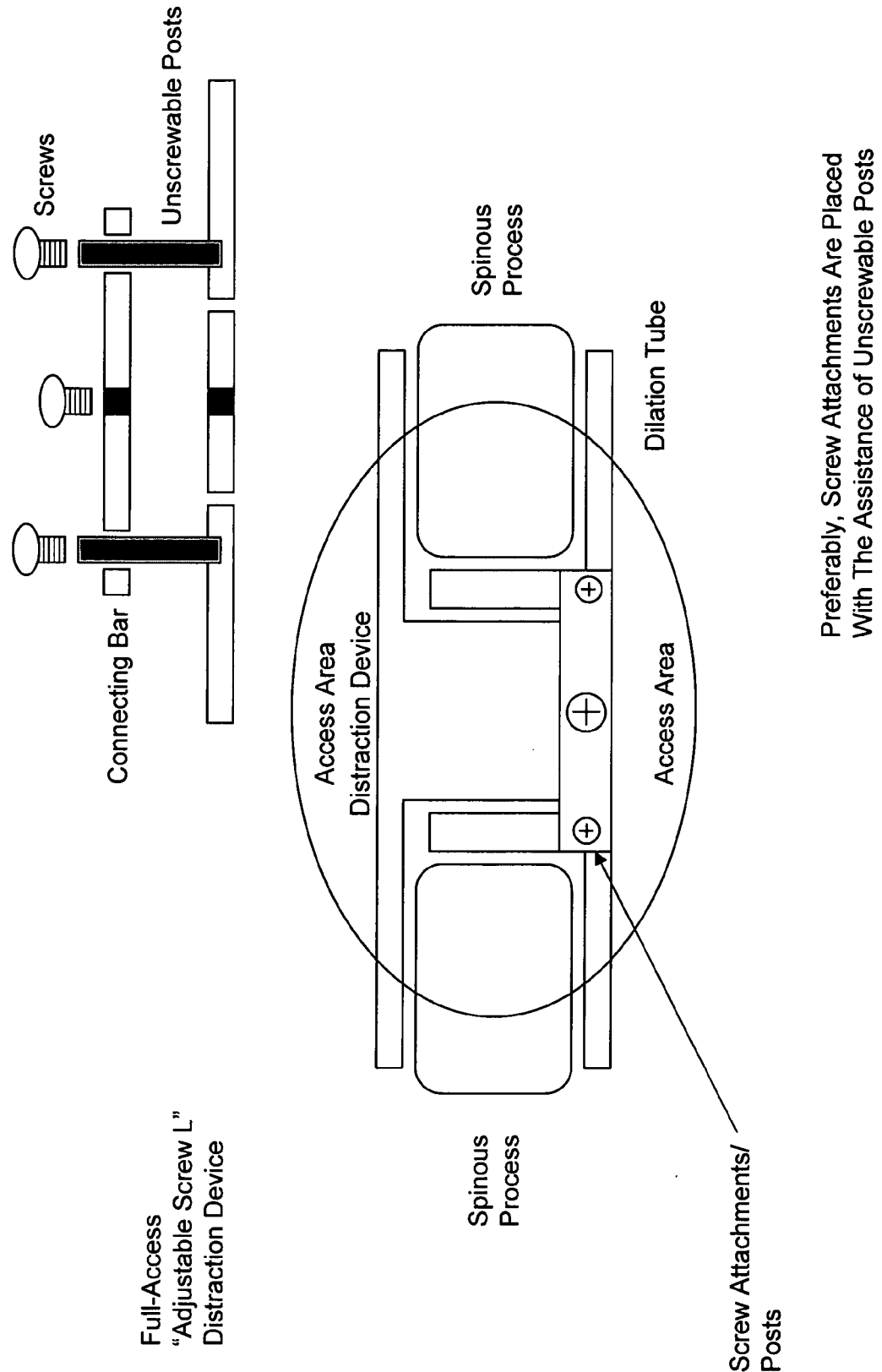
FIG. 42 is a top planar view of a full-access "adjustable screw L" distraction device of the present invention.
Figure 43:
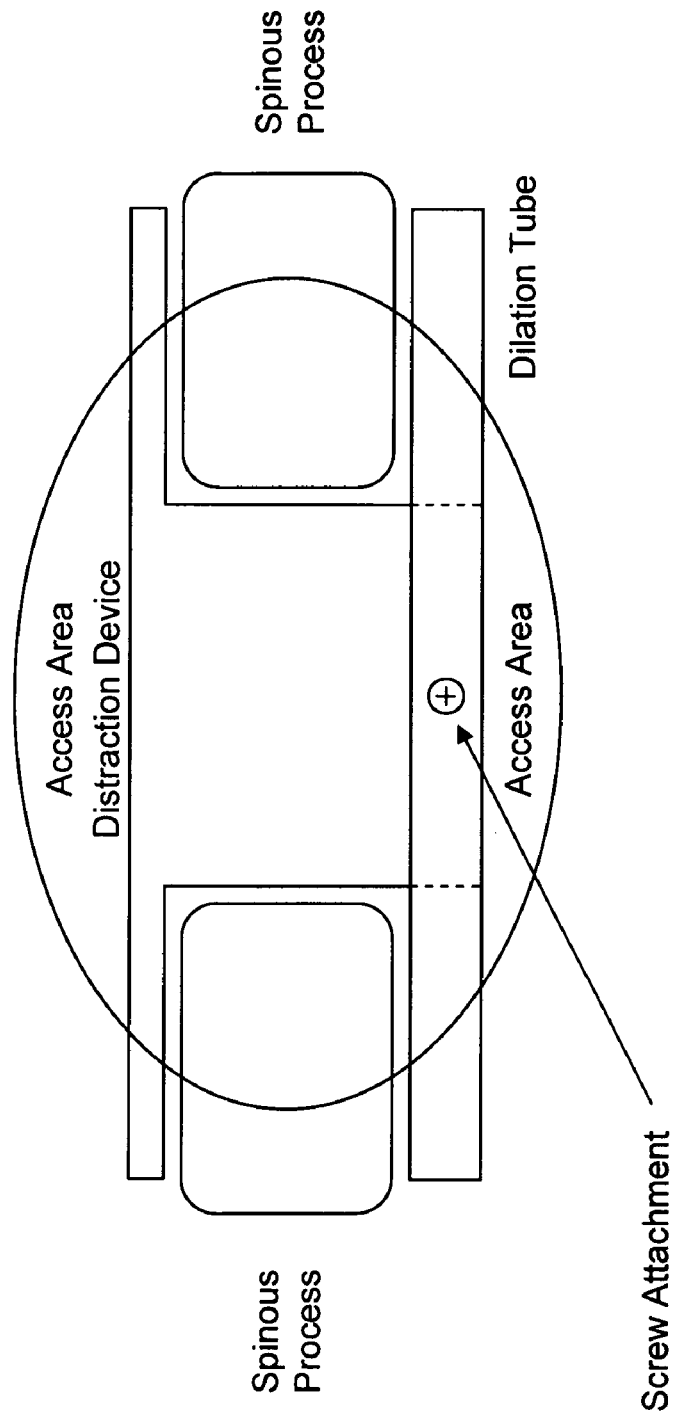
FIG. 43 is a top planar view of a full-access "screw T" distraction device of the present invention.
Figure 44:
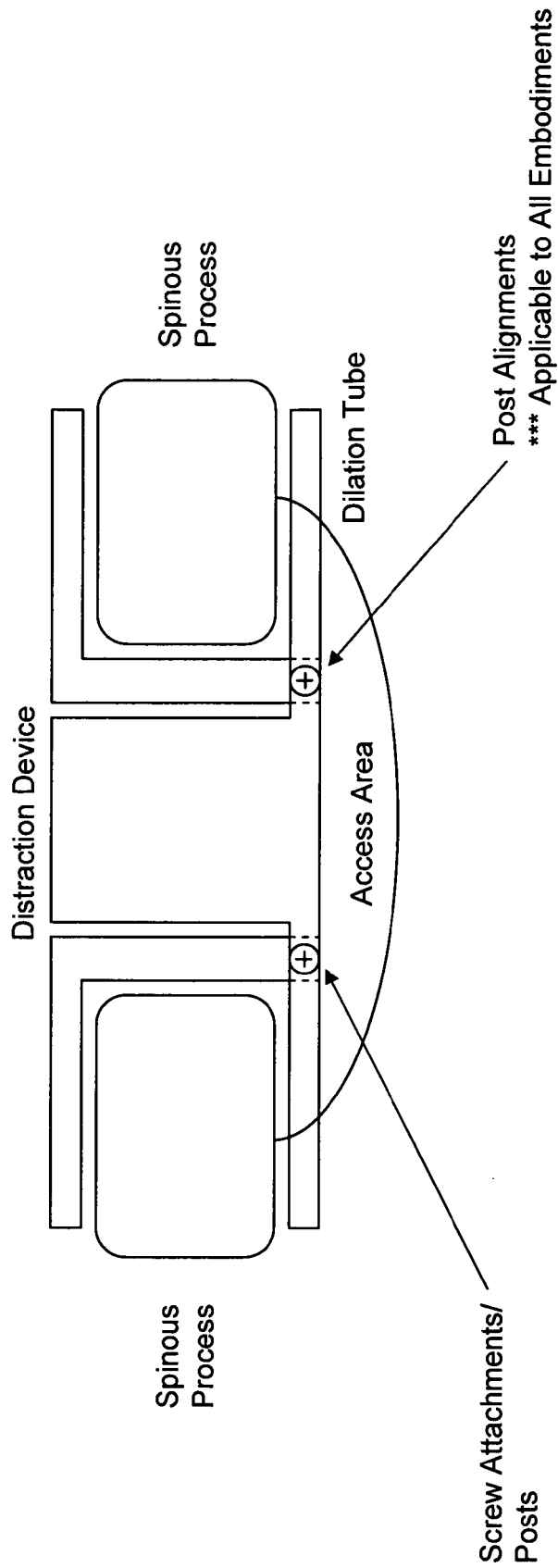
FIG. 44 is a top planar view of a partial-access "screw L" distraction device with post alignment of the present invention.
Figure 45:
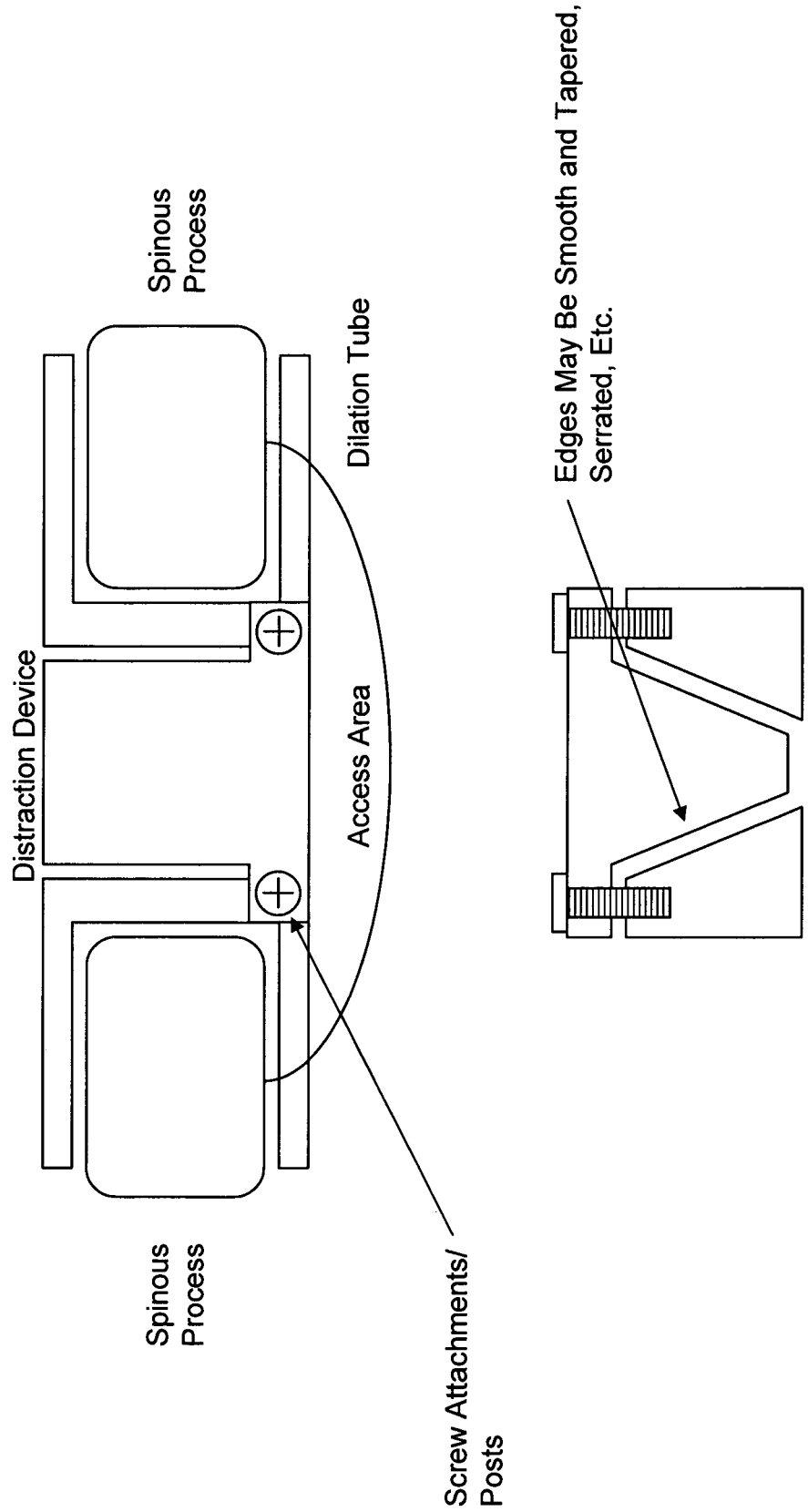
FIG. 45 is a top planar and cross-sectional side view of a partial-access "form-fitting screw T" distraction device of the present invention.
Figure 47:
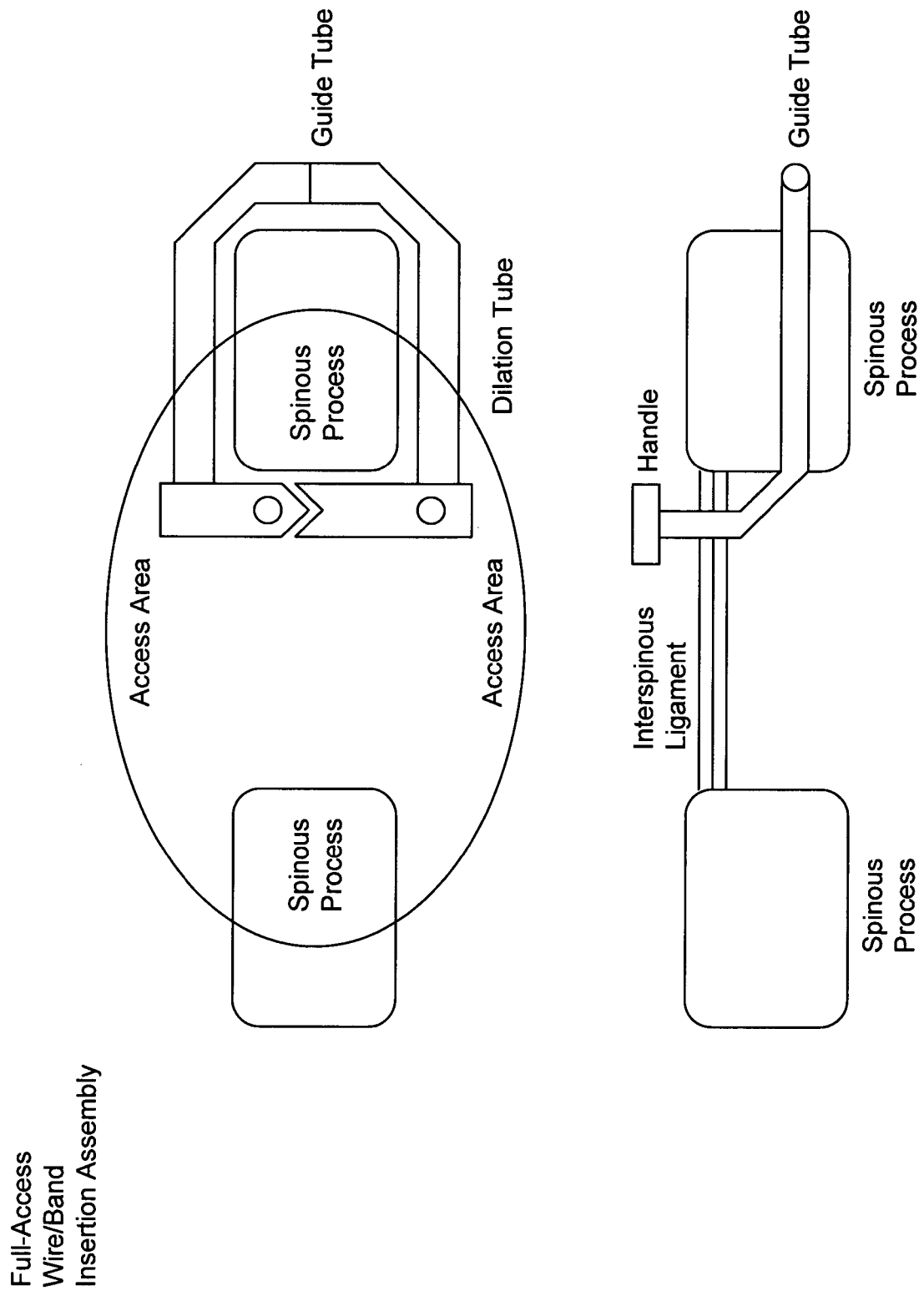
FIG. 47 is a top planar and side planar view of a full-access wire/band insertion assembly of the present invention.
Figure 48:
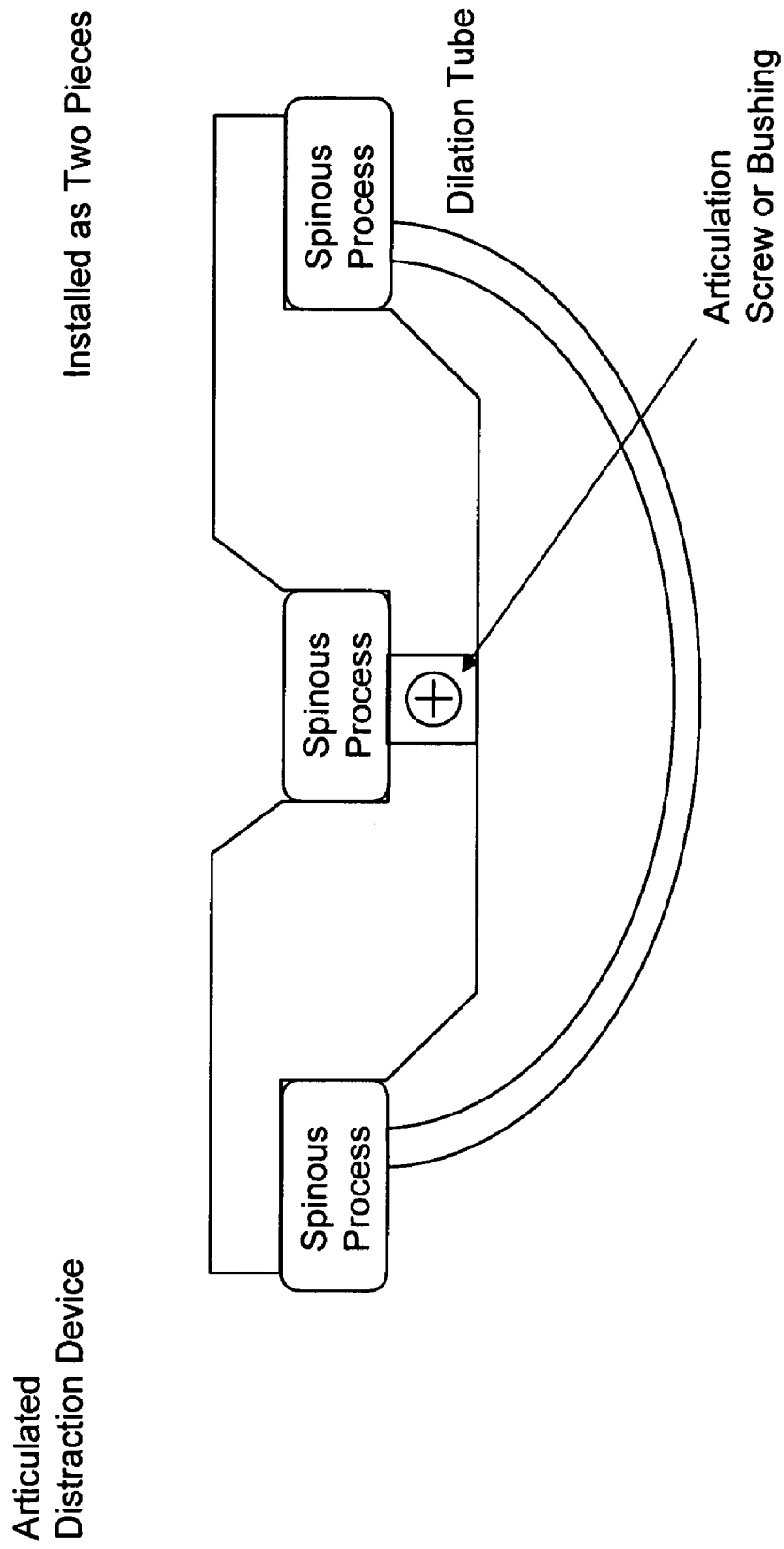
FIG. 48 is a top planar view of an articulated distraction device of the present invention.

Referring now to FIG. 12, an alternative embodiment of an interspinous distraction system and an associated minimally-invasive method of insertion are provided, the interspinous distraction system utilizing a polymer-filled packet and a tension band.

Although the present invention has been illustrated and described with reference to preferred embodiments and examples thereof, it will be readily apparent to those of ordinary skill in the art that other embodiments and examples may perform similar functions and/or achieve similar results. All such equivalent embodiments and examples are within the spirit and scope of the present invention and are intended to be covered by the following claims.

What is claimed is:

1. An interspinous distraction device comprising:
a body assembly configured to be disposed between adjacent spinous processes of the spinal column of a patient, the body assembly having a leading end and a trailing end in opposition to one another defining a thickness, the body assembly defining an axis extending between the leading end and the trailing end, the thickness having a size configured to permit the body assembly to be positioned in a gap between adjacent spinous processes, the body assembly having a top and a bottom in opposition to one another defining a height, the height having a size configured to permit the body assembly to be positioned in the gap between adjacent spinous processes, and the body assembly having a first side and a second side in opposition to one another defining a width, the width having a size configured to permit the body assembly to be positioned in the gap between adjacent spinous processes, wherein the body assembly has a size configured to maintain a separation of the adjacent spinous processes;
a plurality of attachment arms extendable outwardly from the body assembly, at least one of the plurality of attachment arms being extendable outwardly in a direction transverse to the axis and being disposed closer to the leading end than the trailing end, and at least another one of the plurality of attachment arms being extendable outwardly in a direction transverse to the axis and being disposed closer to the trailing end than the leading end, the plurality of attachment arms configured to be disposed about a portion of each of the adjacent spinous processes and securely hold the body assembly in place relative to each of the adjacent spinous processes of the spinal column of the patient; and
a fin structure fixedly attached to at least one of the top and the bottom of the body and extending outwardly from the body between the at least one of the plurality of attachment arms disposed closer to the leading end and the at least another one of the plurality of attachment arms disposed closer to the trailing end, the fin structure is disposed closer to the trailing end than the leading end; and the fin structure has a fixed projection distance from the body assembly that is adapted to stop the body assembly from further insertion into the gap, the at least another one of the plurality of attachment arms being disposed closer to the trailing end having a maximum projection distance from the body greater than the fixed projection distance;
wherein at least a portion of at least one of the body assembly and the plurality of attachment arms comprises a non-planar friction surface disposed on a central weight bearing surface for engaging the adjacent spinous processes of the spinal column of the patient.

2. The interspinous distraction device of claim 1, wherein the non-planar friction surface comprises at least one of a ridged surface, a grooved surface, and a corrugated surface.

3. The interspinous distraction device of claim 1, wherein the height of the body assembly is between about 4 mm and about 20 mm.

4. The interspinous distraction device of claim 1, wherein the width of the body assembly is between about 10 mm and about 25 mm.

5. The interspinous distraction device of claim 1, wherein the thickness of the body assembly is between about 10 mm and about 20 mm.

6. The interspinous distraction device of claim 1, wherein the height of the body assembly is between about 4 mm and about 20 mm, wherein the width of the body assembly is between about 10 mm and about 25 mm, and wherein the thickness of the body assembly is between about 10 mm and about 20 mm.

7. The interspinous distraction device of claim 1, wherein the plurality of attachment arms extendable outwardly from the top and the bottom of the body comprise at least one of the plurality of attachment arms extendable outwardly from the top of the body positioned closer to a first side than a second side and at least another one of the plurality of attachment arms extendable outwardly from the bottom of the body positioned closer to the second side than the first side.

8. An interspinous device comprising:
a body having a leading end and a trailing end in opposition to one another, a top and a bottom in opposition to one another, and a first side and a second side in opposition to one another where the body defines an axis extending between the leading end and the trailing end, wherein the leading end and the trailing end define a thickness of the body, the top and the bottom define a height of the body, and the first side and the second side define a width of the body such that the thickness, the height, and the width are adapted to permit the body to be positioned in a gap between the adjacent spinous processes with the leading end adapted to be disposed on one side of the adjacent spinous processes and the trailing end adapted to be disposed on the other side of the adjacent spinous processes,
a plurality of attachment arms extendable outwardly from the top and the bottom of the body, at least one of the plurality of attachment arms being extendable outwardly in a direction transverse to the axis and being disposed closer to the leading end than the trailing end, and at least another one of the plurality of attachment arms being extendable outwardly in a direction transverse to the axis and being disposed closer to the trailing end than the leading end, the plurality of attachment arms configured to be positioned adjacent a portion of each of the adjacent spinous processes and maintain the body in place between the adjacent spinous processes of the spinal column of the patient;
a first fin structure fixedly attached to one of the top and bottom of the body and extending outwardly from the body in a direction transverse to the axis and between the at least one of the plurality of attachment arms disposed closer to the leading end and the at least another one of the plurality of attachment arms disposed closer to the trailing end, the first fin structure being disposed closer to the trailing end than the leading end; and the first fin structure having a fixed projection distance from the body that is adapted to abut at least one of the adjacent spinous processes to prevent over insertion of the body.

9. The interspinous device of claim 8, wherein the height of the body assembly is between about 4 mm and about 20 mm.

10. The interspinous device of claim 8, wherein the width of the body assembly is between about 10 mm and about 25 mm.

11. The interspinous device of claim 8, wherein the thickness of the body assembly is between about 10 mm and about 20 mm.

12. The interspinous device of claim 8, wherein the height of the body assembly is between about 4 mm and about 20 mm, wherein the width of the body assembly is between about 10 mm and about 25 mm, and wherein the thickness of the body assembly is between about 10 mm and about 20 mm.

13. The interspinous device of claim 8 comprising a second fin structure fixedly attached to the other of the top and bottom of the body.

14. The interspinous device of claim 8, wherein the first fin structure has a fin width less than the width of the body.

15. The interspinous device of claim 14, wherein the plurality of attachment arms have an attachment arm width less than the fin width.

16. The interspinious device of claim 8, wherein the at least another one of the plurality of attachment arms being disposed closer to the trailing end having a maximum projection distance from the body greater than the fixed projection distance.

17. The interspinous device of claim 8, wherein the plurality of attachment arms extendable outwardly from the top and the bottom of the body comprise at least one of the plurality of attachment arms extendable outwardly from the top of the body positioned closer to a first side than a second side and at least another one of the plurality of attachment arms extendable outwardly from the bottom of the body positioned closer to the second side than the first side.

* * * * *